US011815672B2

(12) United States Patent
Hirata

(10) Patent No.: US 11,815,672 B2
(45) Date of Patent: Nov. 14, 2023

(54) OBSERVATION DEVICE

(71) Applicant: Evident Corporation, Nagano (JP)

(72) Inventor: Tadashi Hirata, Tokyo (JP)

(73) Assignee: Evident Corporation, Nagano (JP)

( * ) Notice: Subject to any disclaimer, the term of this patent is extended or adjusted under 35 U.S.C. 154(b) by 717 days.

(21) Appl. No.: 17/015,321

(22) Filed: Sep. 9, 2020

(65) Prior Publication Data

US 2021/0011270 A1     Jan. 14, 2021

Related U.S. Application Data

(63) Continuation of application No. PCT/JP2018/010219, filed on Mar. 15, 2018.

(51) Int. Cl.
| | |
|---|---|
| *G02B 21/00* | (2006.01) |
| *H04N 25/701* | (2023.01) |
| *G01N 33/483* | (2006.01) |
| *G02B 21/26* | (2006.01) |
| *G02B 21/20* | (2006.01) |

(52) U.S. Cl.
CPC ......... *G02B 21/20* (2013.01); *G01N 33/4833* (2013.01); *G02B 21/006* (2013.01); *G02B 21/008* (2013.01); *G02B 21/0032* (2013.01); *G02B 21/0036* (2013.01); *G02B 21/26* (2013.01); *H04N 25/701* (2023.01)

(58) Field of Classification Search
None
See application file for complete search history.

(56) References Cited

U.S. PATENT DOCUMENTS

| | | |
|---|---|---|
| 5,333,066 A | 7/1994 | Sugata |
| 6,906,830 B1 | 6/2005 | Hayashi |
| (Continued) | | |

FOREIGN PATENT DOCUMENTS

| | | |
|---|---|---|
| EP | 2993509 A1 | 3/2016 |
| EP | 3279713 A1 | 2/2018 |
| (Continued) | | |

OTHER PUBLICATIONS

Japanese Office Action dated Sep. 7, 2021 received in 2020-506054.
(Continued)

*Primary Examiner* — Derek S. Chapel
(74) *Attorney, Agent, or Firm* — Scully, Scott, Murphy & Presser, P.C.

(57) ABSTRACT

An observation device includes: first objective lenses arranged in a row so as to be parallel to one another; second objective lenses arranged in a row so as to be parallel to one another; and image capturing elements for capturing first images formed by the first objective lenses and second images formed by the second objective lenses, respectively, wherein each of the objective lenses is a magnifying objective lens, a first axis of light incident on the first objective lenses and a second axis of light incident on the second objective lenses are parallel to one another, fields of view of the first objective lenses and fields of view of the second objective lenses are arranged alternately in a row on an observation line, and the first images and the second images are arranged in a row in image-forming regions that are disposed at positions different from each other.

11 Claims, 18 Drawing Sheets

(56) References Cited

U.S. PATENT DOCUMENTS

| | | |
|---|---|---|
| 2013/0156287 A1 | 6/2013 | Houjou et al. |
| 2015/0055198 A1 | 2/2015 | Kawanishi et al. |
| 2015/0264235 A1 | 9/2015 | Houjou et al. |
| 2016/0048011 A1 | 2/2016 | Suzuki et al. |
| 2017/0355949 A1 | 12/2017 | Hirata et al. |
| 2018/0063355 A1 | 3/2018 | Netsu et al. |

FOREIGN PATENT DOCUMENTS

| | | | |
|---|---|---|---|
| JP | S63-260359 A | 10/1988 | |
| JP | H01-077368 A | 3/1989 | |
| JP | H06-098097 A | 4/1994 | |
| JP | 2856990 B2 | 2/1999 | |
| JP | 2000-216953 A | 8/2000 | |
| JP | 2009-246623 A | 10/2009 | |
| JP | 2014-006291 A | 1/2014 | |
| JP | 2015-041965 A | 3/2015 | |
| JP | 2018-037925 A | 3/2018 | |
| WO | WO-2009122483 A1 * | 10/2009 | ........... H04N 1/0306 |
| WO | WO 2012/029817 A1 | 3/2012 | |
| WO | WO 2014/178294 A1 | 11/2014 | |
| WO | WO 2016/158782 | 10/2016 | |
| WO | WO 2018/051514 A1 | 3/2018 | |

OTHER PUBLICATIONS

International Search Report issued in PCT/JP2018/010219 dated May 29, 2018.

International Search Report and Written Opinion issued in PCT/JP2016/077571 dated Dec. 13, 2016.

* cited by examiner

OBSERVATION DEVICE

CROSS-REFERENCE TO RELATED APPLICATIONS

This is a continuation of International Application PCT/JP2018/010219 which is hereby incorporated by reference herein in its entirety.

TECHNICAL FIELD

The present invention relates to an observation device.

BACKGROUND ART

There are well-known scanning-type image reading devices for capturing an image of a wide area in a short time period by using a line sensor (refer to, for example, PTLs 1 and 2).

CITATION LIST

Patent Literature

{PTL 1}
Publication of Japanese Patent No. 2856990
{PTL 2}
Japanese Unexamined Patent Application, Publication No. 63-260359

SUMMARY OF INVENTION

One aspect of the present invention is an observation device including: a first objective lens group that has a plurality of first objective lenses arranged in a row so as to be parallel to one another, wherein each of the plurality of first objective lenses forms a first image of light coming from a first field of view on an observation line; a second objective lens group that has a plurality of second objective lenses arranged in a row so as to be parallel to one another, wherein each of the plurality of second objective lenses forms a second image of light coming from a second field of view on the observation line; a first image capturing element for capturing plurality of first images formed by the plurality of first objective lenses; and a second image capturing element for capturing plurality of second images formed by the plurality of second objective lenses, wherein each of the plurality of first objective lenses and the plurality of second objective lenses is a magnifying objective lens having a magnification larger than 1, a first axis of light incident on the plurality of first objective lenses and a second axis of light incident on the plurality of second objective lenses are parallel to one another, first fields of view and second fields of view are arranged alternately in a row on the observation line, and the plurality of first images are arranged in a row in a first image-forming region, the plurality of second images are arranged in a row in a second image-forming region, and the first image-forming region and the second image-forming region are disposed at positions that differ from each other.

DESCRIPTION OF EMBODIMENTS

First Embodiment

An observation device 100 according to a first embodiment of the present invention will now be described with reference to the drawings.

Figure 1:
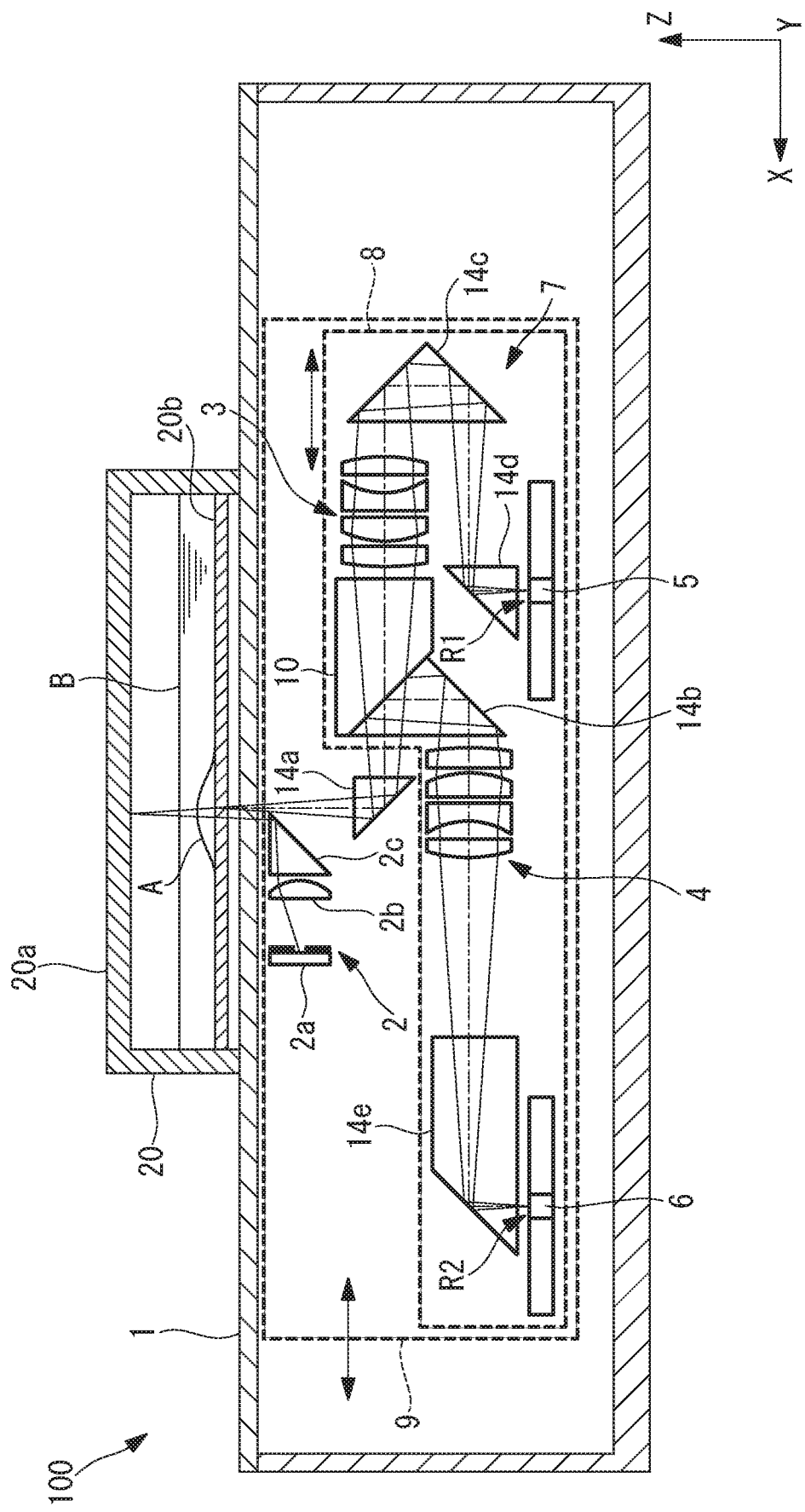
FIG. 1 is a longitudinal sectional view showing the overall configuration of an observation device according to a first embodiment of the present invention.

As shown in FIG. 1, the observation device 100 according to this embodiment includes: a stage 1 for supporting a container 20 that accommodates cells A; two illumination optical systems 2 for irradiating the cells A in the container 20 with illumination light; an image-capturing optical system 7 that has two objective lens groups (objective optical system groups) 3 and 4 and two line sensors 5 and 6 and that capture an image of the cells A; a focus adjusting mechanism 8 for adjusting the focal positions of the objective lens groups 3 and 4; and a scanning mechanism 9 for relatively moving the stage 1 and the image-capturing optical system 7 in a direction along the stage 1.

The container 20 is a hermetically sealed container that is entirely formed of an optically transparent resin, such as a flask or a dish for cell culturing. The container 20 has a top plate 20a and a bottom plate 20b that face each other. The inner-side surface of the top plate 20a is a reflecting surface for Fresnel-reflecting illumination light. The cells A and a culture medium B are accommodated in the container 20.

The stage 1 is an optically transparent flat-plate-shaped member, such as a glass plate, and is disposed horizontally. The container 20 is placed on the stage 1. The illumination optical systems 2, the image-capturing optical system 7, the focus adjusting mechanism 8, and the scanning mechanism 9 are all disposed below the stage 1. The stage 1 may be a top plate of a hermetically sealed, box-shaped housing, so that the illumination optical systems 2, the image-capturing optical system 7, the focus adjusting mechanism 8, and the scanning mechanism 9 can be accommodated in the housing.

In the following description, a vertical direction orthogonal to the stage 1 is defined as a Z direction, and two horizontal directions that are horizontal along the stage 1 and that are orthogonal to each other are defined as an X direction and a Y direction. In particular, the direction (sub-scanning direction) in which the stage 1 and the image-capturing optical system 7 are moved by the scanning mechanism 9 is defined as the X direction.

The illumination optical systems 2 emit illumination light obliquely upward towards the stage 1. More specifically, each of the illumination optical systems 2 includes: a line light source 2a for emitting illumination light in the X direction; a cylindrical lens 2b for converting the illumination light emitted from the line light source 2a into a collimated beam; and a prism 2c that deflects the illumination light coming from the cylindrical lens 2b to emit the illumination light obliquely upward. Illumination light is a line-shaped beam extending in the Y direction. The cylindrical lens 2b has refractive power in the Z direction and does not have refractive power in the X direction and the Y direction. Either one or both of the illumination optical systems 2 are turned on according to the position and the state of the container 20. FIG. 1 shows only one of the illumination optical systems 2.

The illumination light emitted from each of the illumination optical systems 2 passes through the stage 1 and the bottom plate 20b, is reflected at the reflecting surface of the top plate 20a, and is incident on the cells A in fields of view F1 and F2 of the objective lens groups 3 and 4 from obliquely above. Thereafter, the illumination light passes through the cells A, the bottom plate 20b, and the stage 1, is deflected by 90° at a prism 14a, and is incident on the image-capturing optical system 7 along the X direction.

The image-capturing optical system 7 includes: a light dividing element 10; the first objective lens group 3; the second objective lens group 4; the first line sensor 5; and the second line sensor 6.

Figure 2:
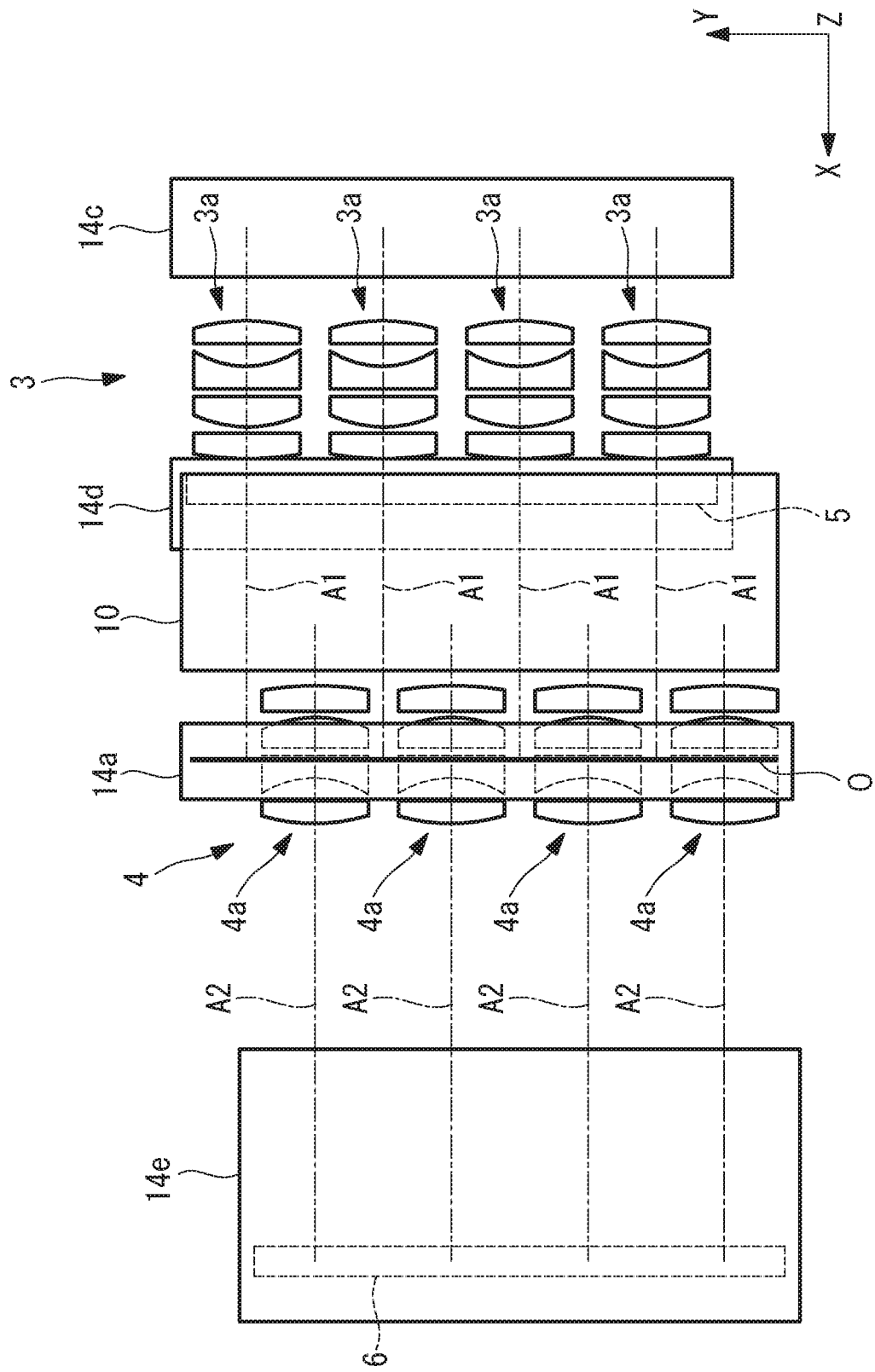
FIG. 2 is a top plan view in the Z direction of an image-capturing optical system of the observation device in FIG. 1.
Figure 3:
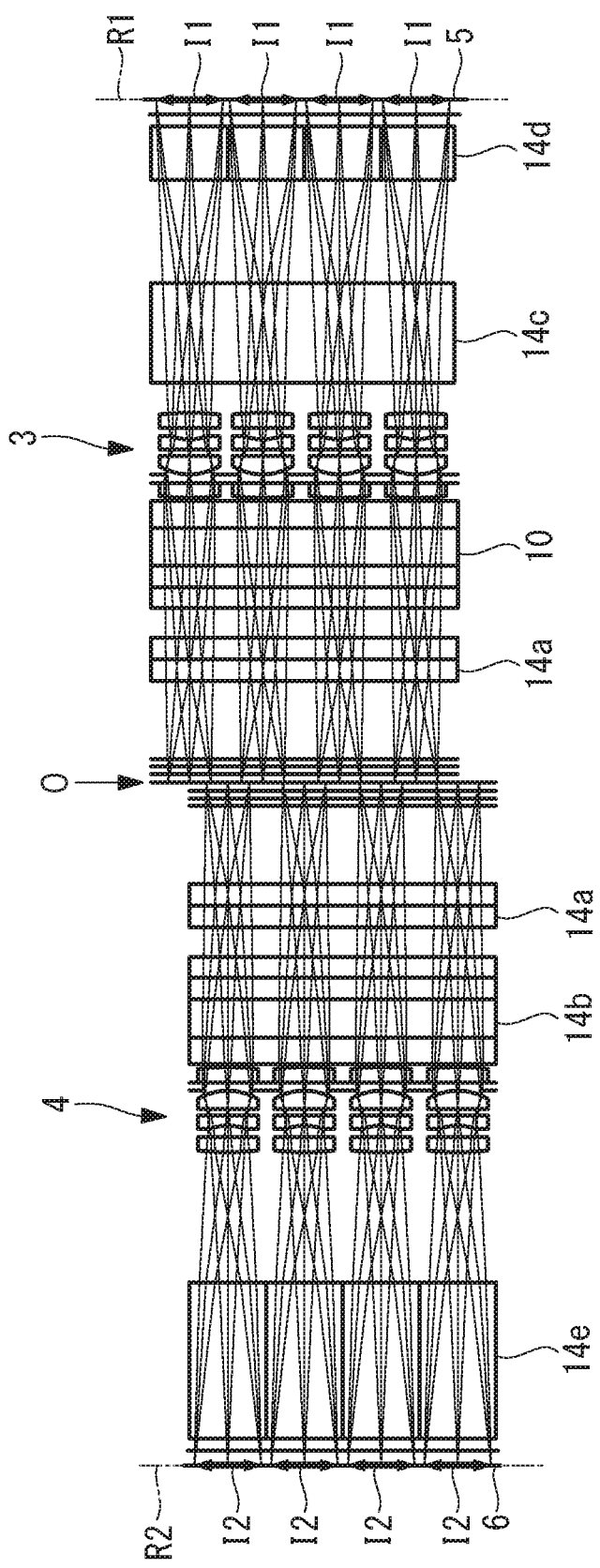
FIG. 3 is a drawing showing optical paths of the image-capturing optical system of the observation device in FIG. 1 when the optical paths are unfolded on a flat surface.

FIG. 2 shows the image-capturing optical system 7 as viewed from above. FIG. 3 shows optical paths from an observation line O to the line sensors 5 and 6 in the form of an unfolded flat surface.

The first objective lens group 3 and the second objective lens group 4 are disposed in regions different from each other. The light dividing element 10 is a half prism or a half mirror and equally divides, to the two objective lens groups 3 and 4, the illumination light that is incident thereon from the prism 14a. FIGS. 1 to 5 show a half prism as the light dividing element 10. The light dividing element 10 transmits, in the X direction, one half portion of the illumination light that is incident thereon and reflects the other half portion in the Z direction, thereby equally splitting into two portions the illumination light that is incident thereon. The one half portion of the light having passed through the light dividing element 10 is incident on the first objective optical system group 3 along the X direction. The other half portion of the light having been reflected at the light dividing element 10 is bent by 90° at a prism 14b and is incident on the second objective optical system group 4 along the X direction.

As shown in FIGS. 2 and 3, the first objective lens group 3 includes four first objective lenses (first objective optical systems) 3a. The four first objective lenses 3a are arranged in a row in the Y direction so as to be parallel to one another, and each of the first objective lenses 3a is disposed along the X direction. The optical axes on the light entry side (object side) of the four first objective lenses 3a are bent by 90° at the prism 14a, so that the focal planes of the four first objective lenses 3a are disposed above the stage 1.

Each of the first objective lenses 3a collects the light from the first field of view F1 on the corresponding focal plane to form an image of the collected light as a first image I1. The light emitted from the four objective lenses 3a is guided to a first image-forming region R1 by prisms 14c and 14d, and the four first images I1 are formed in the first image-forming region R1. The first image-forming region R1 is a planar region orthogonal to the Z direction. The four first fields of view F1 are arranged in a row on the observation line O extending in the Y direction, and the four first images I1 are arranged in a row in the Y direction in the first image-forming region R1.

The second objective lens group 4 includes four second objective lenses (second objective optical systems) 4a. The four second objective lenses 4a are arranged in a row in the Y direction so as to be parallel to one another, and each of the second objective lenses 4a is disposed along the X direction. The optical axes on the light entry side (object side) of the four second objective lenses 4a are bent by 180° at the prism 14b and are further bent by 90° at the prism 14a, so that the focal planes of the four second objective lenses 4a are disposed above the stage 1.

Each of the second objective lenses 4a collects the light from the second field of view F2 on the corresponding focal plane to form an image of the collected light as a second image I2. The light emitted from the four objective lenses 4a is guided to a second image-forming region R2 by a prism 14e, and the four second images I2 are formed in the second image-forming region R2. The second image-forming region R2 is a planar region orthogonal to the Z direction and is disposed at a position different from the position at which the first image-forming region R1 is disposed. The four second fields of view F2 are arranged in a row on the observation line O extending in the Y direction, and the four second images I2 are arranged in a row in the Y direction in the second image-forming region R2.

Here, the first fields of view F1 and the second fields of view F2 are arranged in a row on the same observation line O.

Figure 4:
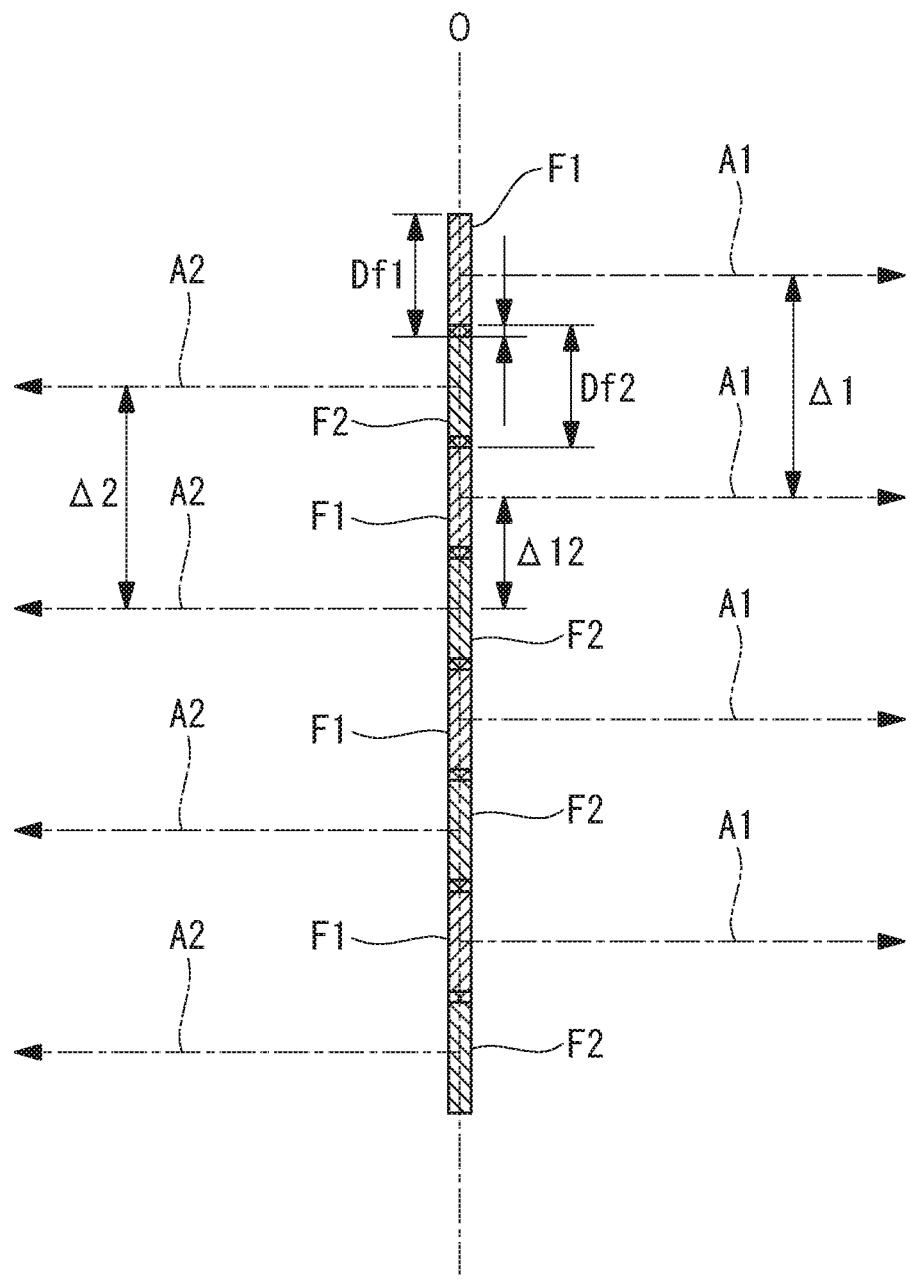
FIG. 4 is a drawing for illustrating the arrangement of first fields of view and second fields of view on an observation line.

In addition, as shown in FIG. 2, a Y-direction spacing Δ1 between the optical axes A1 of neighboring first objective lenses 3a and a Y-direction spacing Δ2 between the optical axes A2 of neighboring second objective lenses 4a are identical to each other. Furthermore, each of the optical axes A1 and the corresponding optical axis A2 are offset from each other in the Y direction by a distance Δ12, which is smaller than the spacings Δ1 and Δ2. By doing so, the optical axes A1 and the optical axes A2 are alternately arranged in the Y direction in top XY plan view, and the first fields of view F1 and the second fields of view F2 are alternately arranged on the observation line O, as shown in FIG. 4. Y-direction widths Df1 and Df2 of the respective fields of view F1 and F2 are larger than the spacing Δ12 between optical axes A1 and A2 that are adjacent to each other in the Y direction. By doing so, end sections of a first field of view F1 and a second field of view F2 that are adjacent to each other in the Y direction overlap each other.

Figure 5:
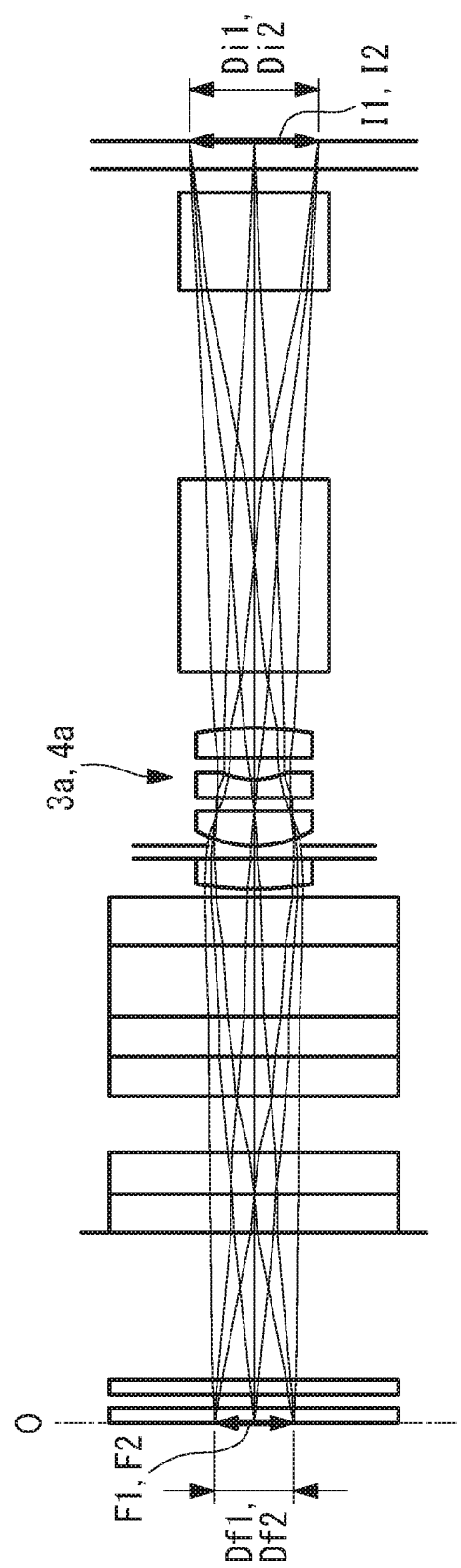
FIG. 5 is a drawing for illustrating the magnifications of a first objective lens and a second objective lens, as well as field-of-view widths and image widths.

As shown in FIG. 5, each of the first objective lenses 3a and each of the second objective lenses 4a are magnifying objective lenses (magnifying objective optical systems) having a magnification larger than 1. Therefore, Y-direction widths Di1 and Di2 of the respective images I1 and I2 are larger than the Y-direction widths Df1 and Df2 of the respective fields of view F1 and F2. The magnifications and the spacings Δ1 for the first objective lenses 3a are designed so that the spacing Δ1 between neighboring optical axes A1 becomes larger than the width Di1 of each of the first images I1. By doing so, first images I1 that are adjacent to each other in the first image-forming region R1 are completely spatially separated. Likewise, the magnifications and the spacings Δ2 for the second objective lenses 4a are designed so that the spacing Δ2 between neighboring optical axes A2 is larger than the width Di2 of each of the second images I2. By doing so, second images I2 that are adjacent to each other in the second image-forming region R2 are completely spatially separated.

The first line sensor 5 is a one-dimensional image capturing element having a plurality of pixels arranged in a row in the Y direction and is disposed in the first image-forming region R1. The first line sensor 5 captures the four first images I1 in the first image-forming region R1 to acquire a first one-dimensional image.

The second line sensor 6 is a one-dimensional image capturing element having a plurality of pixels arranged in a row in the Y direction and is disposed in the second image-forming region R2. The second line sensor 6 captures the four second images I2 in the second image-forming region R2 to acquire a second one-dimensional image.

The focus adjusting mechanism 8 moves, by means of, for example, a linear actuator (not shown in the figure), the entire image-capturing optical system 7 in the X direction relative to the stage 1 and the prism 14a. As a result of the image-capturing optical system 7 being moved in the X direction, the focal point of each of the objective lenses 3a and 4a, i.e., the observation line O, moves in the Z direction relative to the cells A in the container 20. By doing so, it is possible to adjust the focal positions of the objective lenses 3a and 4a relative to the cells A and align the focal points with the cells A.

The scanning mechanism 9 integrally moves, by means of, for example, a linear actuator (not shown in the figure), the illumination optical systems 2, the image-capturing optical system 7, and the prism 14a in the X direction relative to the stage 1. As a result of the image-capturing optical system 7 and the prism 14a being moved in the X direction, the fields of view F1 and F2 and the observation line O move in the X direction relative to the cells A. In addition, the area illuminated by each of the illumination optical systems 2 also moves in the X direction as the fields of view F1 and F2 move, and the fields of view F1 and F2 are illuminated with illumination light regardless of the X-direction position of the image-capturing optical system 7.

The scanning mechanism 9 may move the stage 1 in the X direction, instead of moving the illumination optical systems 2, the image-capturing optical system 7, and the prism 14a. Alternatively, the scanning mechanism 9 may move the stage 1 in the X direction, in addition to the illumination optical systems 2, the image-capturing optical system 7, and the prism 14a.

Next, the operation of the observation device 100 will be described by way of an example where the cells A being cultured in the container 20 are observed.

The observation device 100 is disposed in a cell culture device, such as an incubator, together with the container 20 placed on the stage 1. The observation device 100 acquires images of the cells A in the container 20 according to, for example, a preset schedule.

More specifically, line-shaped illumination light is emitted obliquely upward from an illumination optical system 2. The illumination light passes through the stage 1 and the bottom plate 20b, is reflected obliquely downward at the reflecting surface of the top plate 20a, passes through the cells A, the bottom plate 20b, and the stage 1, is deflected at the prism 14a, and is incident on the image-capturing optical system 7.

In the image-capturing optical system 7, the illumination light is divided by the light dividing element 10 to the first objective lens group 3 and the second objective lens group 4. The illumination light that is incident on the four objective lenses 3a of the first objective lens group 3 forms images in the first image-forming region R1, and the illumination light that is incident on the four objective lenses 4a of the second objective lens group 4 forms images in the second image-forming region R2. Here, the illumination light is incident on the objective lenses 3a and 4a obliquely relative to the optical axes A1 and A2. Therefore, shaded images I1 and I2 of the cells A are formed in the first and second image-forming regions R1 and R2, respectively.

The four first images I1 in the first image-forming region R1 are captured by the first line sensor 5, and a first one-dimensional image of the cells A is acquired. The four second images I2 in the second image-forming region R2 are captured by the second line sensor 6, and a second one-dimensional image of the cells A is acquired.

While moving in the X direction through the operation of the scanning mechanism 9, the image-capturing optical system 7 repeats the acquisition of one-dimensional images by means of the first line sensor 5 and the second line sensor 6. By doing so, two-dimensional images of the cells distributed over the bottom plate 20b are acquired by the first line sensor 5 and the second line sensor 6.

Figure 6:
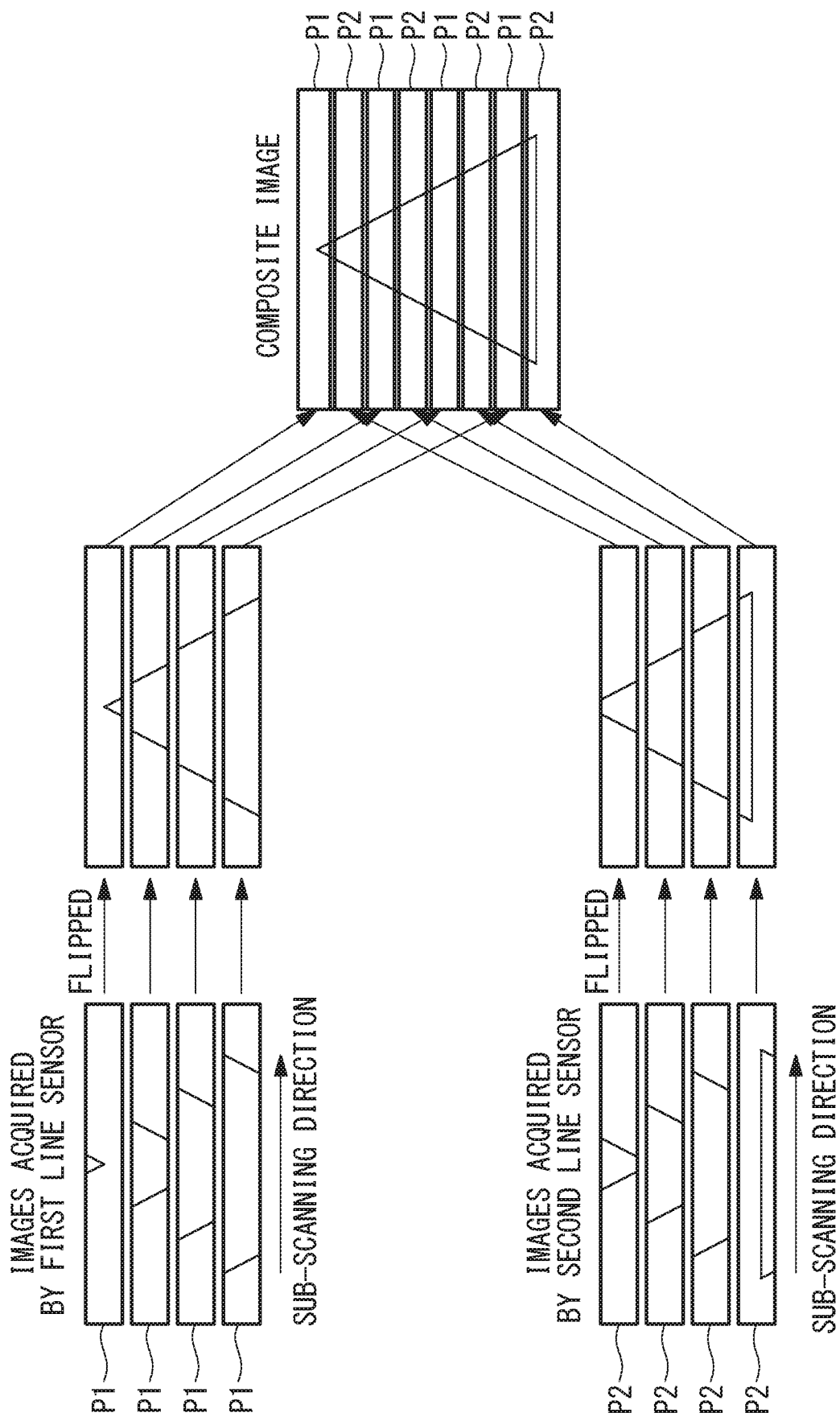
FIG. 6 is a drawing for illustrating a method for processing images acquired by a first line sensor and a second line sensor of the observation device in FIG. 1.

As shown in FIG. 6, the two-dimensional image acquired by the first line sensor 5 is composed of four first partial images P1 corresponding to the respective four first objective lenses 3a. The two-dimensional image acquired by the second line sensor 6 is composed of four second partial images P2 corresponding to the respective four second objective lenses 4a. Because the images I1 and I2 formed by the objective lenses 3a and 4a are inverted images, the partial images P1 and P2 appear upside down. In order to correct the upside-down images, the partial images P1 and P2 are subjected to processing for flipping the images in a direction orthogonal to the sub-scanning direction.

Subsequently to the flipping, a single two-dimensional composite image is generated by alternately arranging the first partial images P1 and the second partial images P2 and then joining the partial images P1 and P2. Here, because each of the first fields of view F1 and a neighboring second field of view F2 overlap each other at end sections thereof, the edge section of each of the first partial images P1 and the edge of a neighboring second partial image P2 overlap each other when the partial images P1 and P2 are joined. By doing so, a composite image that is seamless in a main scanning direction, which is parallel to the observation line O, can be generated.

In this manner, this embodiment provides an advantage in that images of a wide area, such as the entire bottom plate 20b of the container 20, can be acquired in a short time period by scanning the illumination optical systems 2, the image-capturing optical system 7, and the prism 14a relative to the cells A.

This embodiment also provides an advantage in that the Z-direction width of the observation device 100 can be reduced by disposing the illumination optical systems 2, the image-capturing optical system 7, the focus adjusting mechanism 8, and the scanning mechanism 9 all below the stage 1.

In addition, because the eight objective lenses 3a and 4a are arranged in the Y direction, which is the main scanning direction, and images of an image-capturing area in the main scanning direction are captured by using the eight objective lenses 3a and 4a, the optical distances from the cells A to the line sensors 5 and 6 become small, compared with the case where a single objective lens is used. This provides an advantage in that the image-capturing optical system 7 can be made compact.

In addition, high-resolution first images I1 and second images I2 are formed by using magnifying objective lenses as the objective lenses 3a and 4a. This provides an advantage in that high-resolution images of the cells A can be acquired.

In addition, the first objective lens group 3 and the second objective lens group 4 are disposed so that the first fields of view F1 and the second fields of view F2 are alternately arranged on the observation line O, and the first images I1 of the first objective lens group 3 and the second images I2 of the second objective lens group 4 are formed in the image-forming regions R1 and R2 that differ from each other. Therefore, the spacing Δ1 between neighboring optical axes A1 in the first image-forming region R1 and the spacing Δ2 between neighboring optical axes A2 in the second image-forming region R2 become larger than the spacing Δ12 between an optical axis A1 and a neighboring optical axis A2 on the observation line O. By doing so, the image-capturing optical system 7 can be easily designed so that each of the first fields of view F1 and a neighboring second field of view F2 partially overlap each other and so that neighboring first images I1 do not overlap each other and neighboring second images I2 do not overlap each other.

A design example of the image-capturing optical system 7 in this embodiment will be described below.

All of the objective lenses 3a and 4a have the same specifications. Regarding the objective lenses 3a and 4a, the magnification is 1.6, the NA (numerical aperture) is 0.11, the widths Df1 and Df2 of the fields of view F1 and F2 on the observation line O are 5.6 mm, and the widths Di1 and Di2 of the images I1 and I2 are 8.96 mm. The Y-direction spacing Δ1 between the optical axes A1 of neighboring first objective lenses 3a is 10 mm, and the Y-direction spacing Δ2 between the optical axes A2 of neighboring second objective lenses 4a is 10 mm. Each of the optical axes A1 and the corresponding optical axis A2 are offset by 5 mm from each other in the Y direction, and therefore, the spacing Δ12 between optical axes A1 and A2 that are adjacent to each other in the Y direction is 5 mm.

The line sensors 5 and 6 have the same specifications. Regarding the line sensors 5 and 6, the pixel pitch is 3.5 μm, the number of pixels is 11140, and the effective length is 39.025 mm.

With the above-described design, fields of view F1 and F2 that are adjacent to each other overlap each other by 0.6 mm. Therefore, it is possible to observe an entire image-capturing area as wide as 40.6 mm seamlessly. In addition, because the spacing Δ1 between neighboring optical axes A1 is larger than the width Di1 of each of the first images I1, first images I1 that are adjacent to each other are completely spatially separated without overlapping each other. Similarly, second images I2 that are adjacent to each other are completely spatially separated without overlapping each other.

Although, in this embodiment and the design example thereof, the objective lens groups 3 and 4 include the four objective lenses 3a and 4a, respectively, instead of this, the number of objective lenses 3a and the number of objective lenses 4a may be an arbitrary number equal to or larger than 2.

Second Embodiment

Next, an observation device 200 according to a second embodiment of the present invention will be described with reference to the drawings.

In this embodiment, configurations different from those in the first embodiment will be described. Also, configurations in common with those in the first embodiment will be denoted with the same reference signs and descriptions thereof will be omitted.

Figure 7:
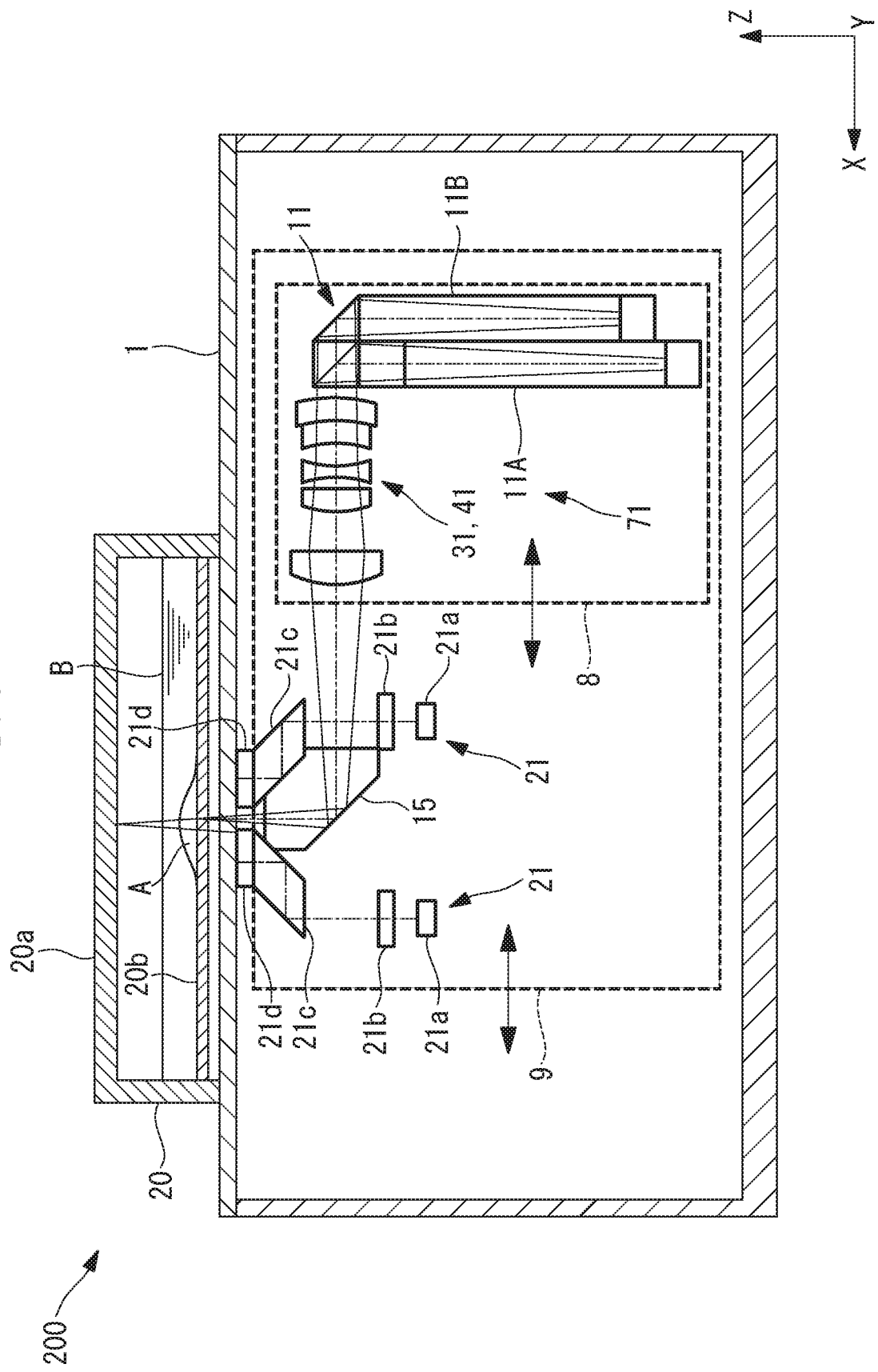
FIG. 7 is a longitudinal sectional view showing the overall configuration of an observation device according to a second embodiment of the present invention.

As shown in FIG. 7, the observation device 200 according to this embodiment includes the stage 1, two illumination optical systems 21, an image-capturing optical system 71, the focus adjusting mechanism 8, and the scanning mechanism 9.

The illumination optical systems 21 emit line-shaped illumination light obliquely upward towards the stage 1. More specifically, each of the illumination optical systems 21 includes: a plurality of LED light sources 21a arranged in a row in the Y direction; a linear Fresnel lens 21b; a prism 21c for deflecting obliquely upward the light emitted from the linear Fresnel lens 21b; and a light-diffusing plate 21d for diffusing a plurality of light rays emitted from the prism 21c. As a result of the plurality of light rays arranged in the Y direction being diffused by the light-diffusing plate 21d, line-shaped illumination light having substantially uniform brightness is generated. In the same manner as in the first embodiment, either one or both of the illumination optical systems 21 are turned on according to the position and the state of the container 20.

The illumination light emitted from each of the illumination optical systems 21 passes through the stage 1 and the bottom plate 20b, is reflected at the reflecting surface of the top plate 20a, and is incident from obliquely above on the cells A in the fields of view F1 and F2 of objective lens groups 31 and 41. Thereafter, the illumination light passes through the cells A, the bottom plate 20b, and the stage 1, is deflected by 90° at a prism 15, and is incident on the image-capturing optical system 71 along the X direction.

The image-capturing optical system 71 includes: the first objective lens group 31; the second objective lens group 41; the first line sensor 5; the second line sensor 6; and an optical-path separating optical system 11.

Figure 8:
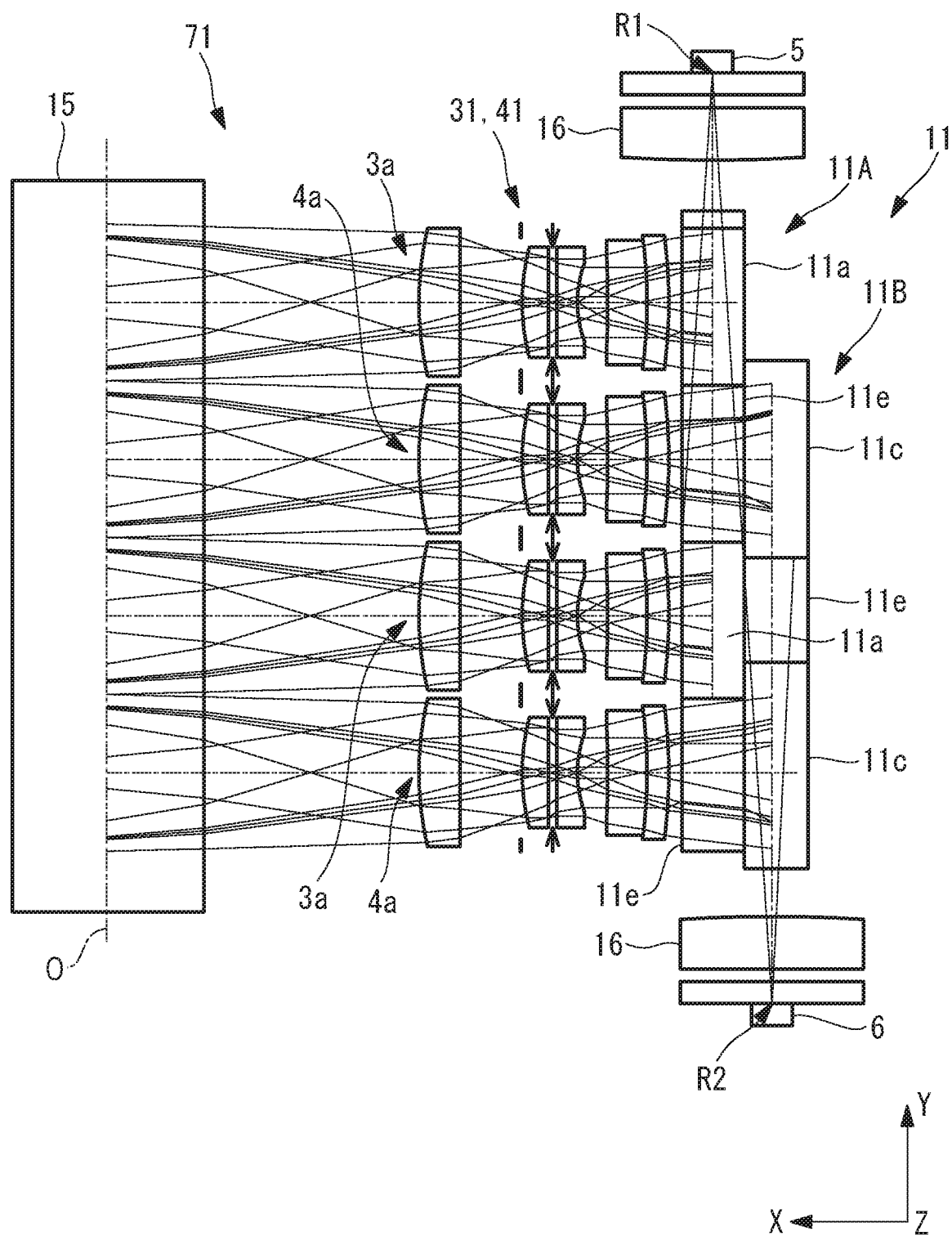
FIG. 8 is a top plan view in the Z direction of an image-capturing optical system of the observation device in FIG. 7.

As shown in FIG. 8, the first objective lens group 31 includes two first objective lenses 3a, and the second objective lens group 41 includes two second objective lenses 4a. The first objective lenses 3a and the second objective lenses 4a are alternately arranged in a row in the Y direction so as to be parallel to one another, and each of the first objective lenses 3a and 4a is disposed along the X direction. In other words, the first objective lens group 31 and the second objective lens group 41 are disposed in the same region. The optical axes on the light entry side (object side) of the four objective lenses 3a and 4a are bent by 90° at the prism 15, so that the focal planes of the four objective lenses 3a and 4a are disposed above the stage 1. The first fields of view F1 and the second fields of view F2 are arranged alternately in a row on the observation line O.

Because the four objective lenses 3a and 4a are disposed on the same plane, the light emitted from the first objective lenses 3a and the light emit from the second objective lenses 4a are alternately arranged on the same plane. The optical-path separating optical system 11 separates, into different planes, the light emitted from the first objective lenses 3a and the light emitted from the second objective lenses 4a.

Figure 9A:
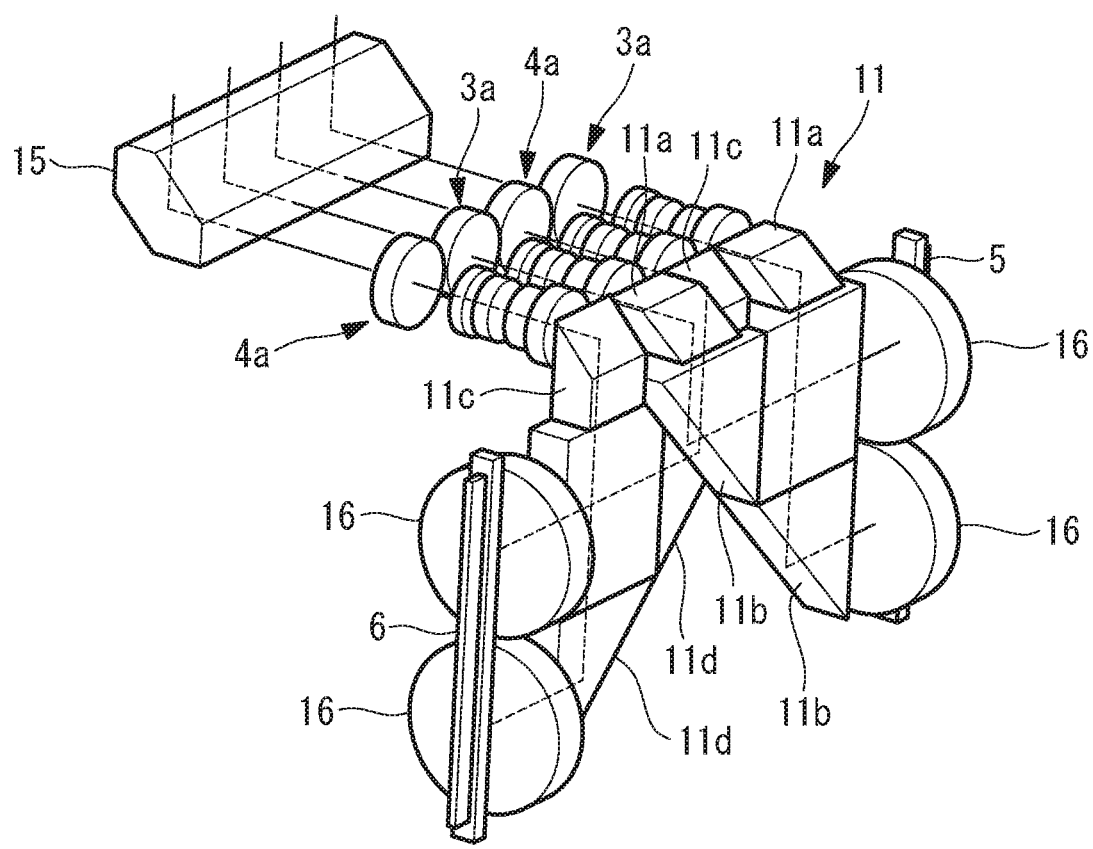
FIG. 9A is a perspective view of an optical-path separating optical system of the image-capturing optical system in FIG. 8.
Figure 9B:
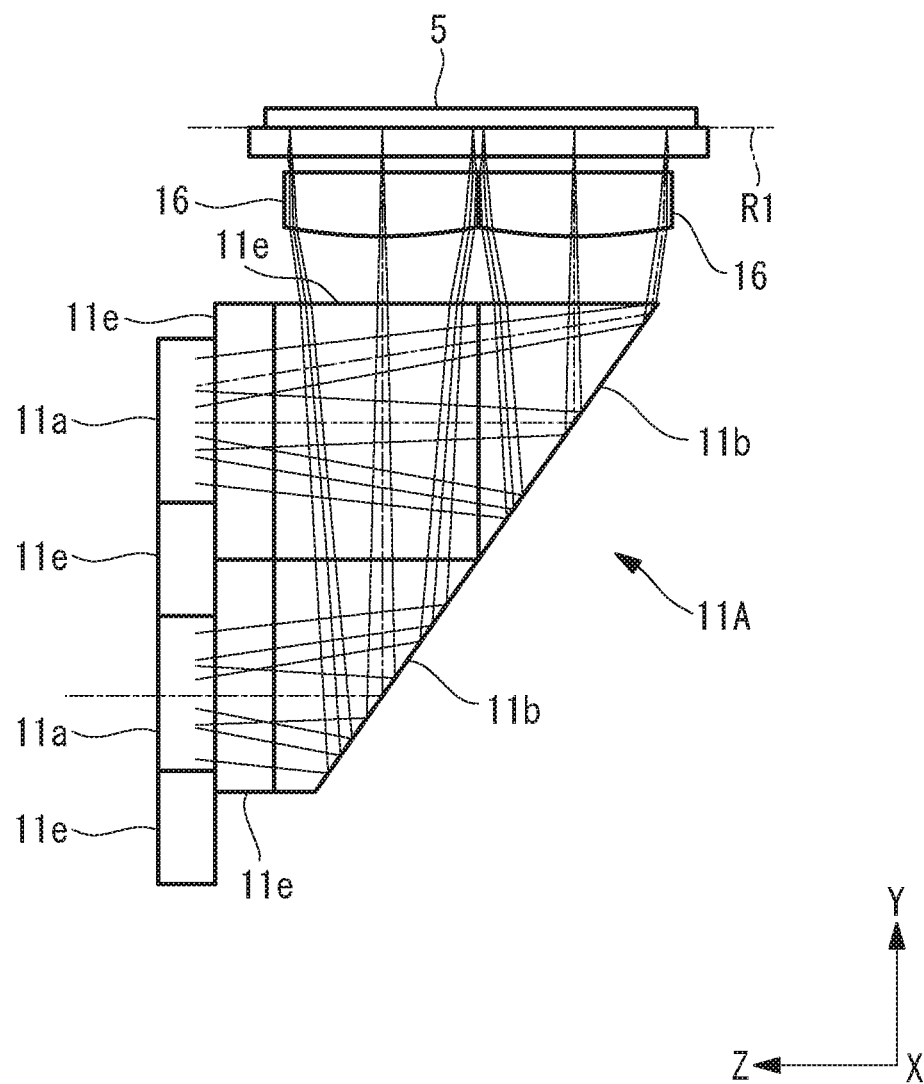
FIG. 9B is a side elevational view of a first prism group of the optical-path separating optical system of the image-capturing optical system in FIG. 8, as viewed from the right side along the X direction.
Figure 9C:
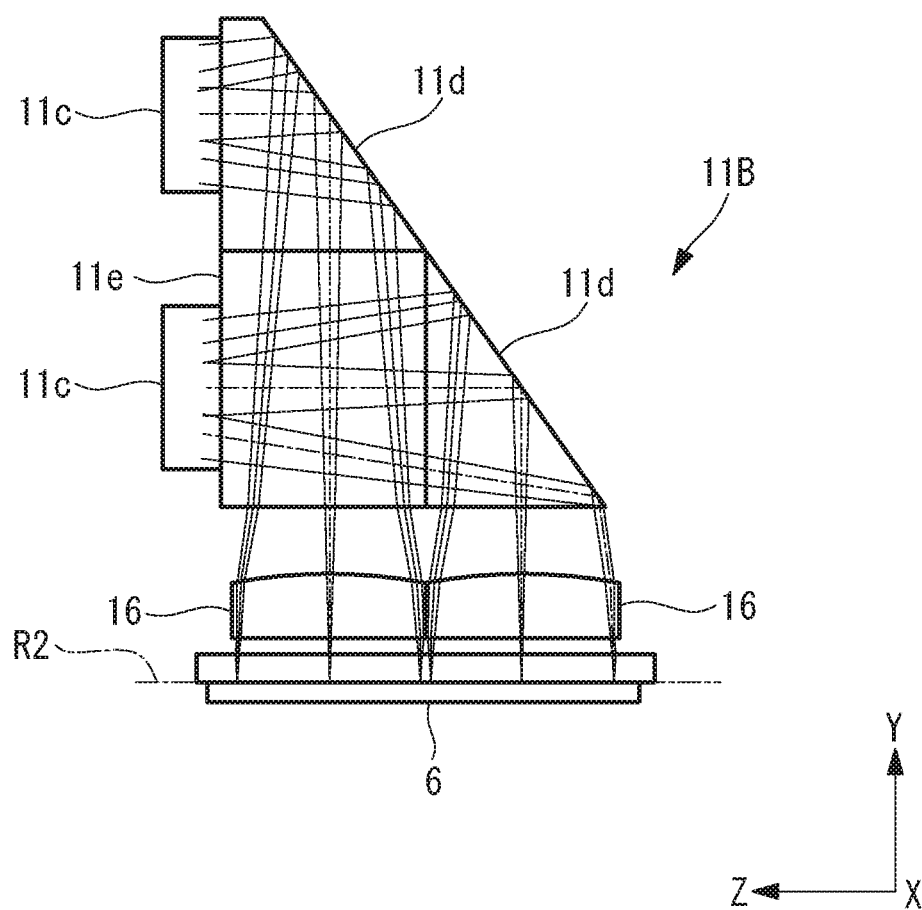
FIG. 9C is a side elevational view of a second prism group of the optical-path separating optical system of the image-capturing optical system in FIG. 8, as viewed from the right side along the X direction.

More specifically, as shown in FIGS. 9A to 9C, the optical-path separating optical system 11 includes: a first prism group (first deflecting element group) 11A; and a second prism group (second deflecting element group) 11B.

As shown in FIG. 9B, the first prism group 11A includes two prisms 11a for deflecting, in the Z direction, the two light rays emitted along the X direction from the two first objective lenses 3a; and two prisms 11b for deflecting, in the Y direction, the two light rays deflected by the two prisms 11a. As shown in FIG. 9C, the second prism group 11B includes two prisms 11c for deflecting, in the Z direction, the two light rays emitted along the X direction from the two second objective lenses 4a; and two prisms 11d for deflecting, in the Y direction, the two light rays deflected by the two prisms 11c. Reference numeral 11e denotes parallel plates.

The two prisms 11a are arranged in the Y direction, and the two prisms 11c are arranged in the Y direction. In addition, the prisms 11a and the prisms 11c are disposed at positions that differ from each other in the X-direction. Therefore, the light emitted from the first objective lenses 3a and the light emitted from the second objective lenses 4a are separated by the prisms 11a and the prisms 11c into different planes that are separated from each other in the X direction.

Subsequently, the Y-direction light emitted from the first objective lenses 3a is rearranged by the prisms 11b to light along the Z direction. Similarly, the Y-direction light emitted from the second objective lenses 4a is rearranged by the prisms 11d to light along the Z direction. Here, the prisms 11b and prisms 11d deflect the light in directions opposite to each other. Therefore, the first image-forming region R1 in which the first images I1 are formed and the second image-forming region R2 in which the second images I2 are formed are disposed at positions that are separated from each other in the Y direction. In this embodiment, the first image-forming region R1 and the second image-forming region R2 are planar regions orthogonal to the Y direction. The first line sensor 5 is disposed in the first image-forming region R1 along the Z direction, and the second line sensor 6 is disposed in the second image-forming region R2 along the Z direction. Field lenses 16 are disposed immediately before each of the line sensors 5 and 6.

Next, the operation of the observation device 200 will be described by way of an example where the cells A being cultured in the container 20 are observed.

The observation device 200 is disposed in a cell culture device, such as an incubator, together with the container 20 placed on the stage 1. The observation device 200 acquires images of the cells A in the container 20 according to, for example, a preset schedule.

More specifically, line-shaped illumination light is emitted obliquely upward from an illumination optical system 21. The illumination light passes through the stage 1 and the bottom plate 20b, is reflected obliquely downward at the reflecting surface of the top plate 20a, passes through the cells A, the bottom plate 20b, and the stage 1, is deflected at the prism 15, and is incident on the image-capturing optical system 71.

In the image-capturing optical system 71, the illumination light is incident on the first and second objective lens groups 31 and 41. Thereafter, the illumination light emitted from the objective lenses 3a of the first objective lens group 31 and the illumination light emitted from the objective lenses 4a of the second objective lens group 41 are separated by the optical-path separating optical system 11 into different planes and form images in different image-forming regions R1 and R2. Here, the illumination light is incident on the objective lenses 3a and 4a obliquely relative to the optical axes A1 and A2. Therefore, shaded images I1 and I2 of the cells A are formed in the first and second image-forming regions R1 and R2, respectively.

Thereafter, in the same manner as in the first embodiment, two-dimensional images are acquired by the line sensors 5 and 6, and a composite image is generated.

This embodiment provides the following advantages, in addition to the advantages provided by the first embodiment. More specifically, because the light dividing element 10, such as a half prism or a half mirror, is not used in the second embodiment, the first images I1 and the second images I2 become brighter than those in the first embodiment. Therefore, the second embodiment provides an advantage in that the exposure times of the line sensors 5 and 6 can be reduced, whereby images of the entire container 20 can be acquired in a shorter time period. Alternatively, the second embodiment provides an advantage in that power can be saved by reducing the amount of illumination light.

A design example of the image-capturing optical system 71 in this embodiment will be described below.

All of the objective lenses 3a and 4a have the same specifications. Regarding the objective lenses 3a and 4a, the magnification is 1.8, the NA (numerical aperture) is 0.11, the widths Df1 and Df2 of the fields of view F1 and F2 on the observation line O are 11.6 mm, and the widths Di1 and Di2 of the images I1 and I2 are 20.88 mm. The Y-direction spacing Δ1 between the optical axes A1 of the first objective lenses 3a is 22 mm, and the Y-direction spacing Δ2 between the optical axes A2 of the second objective lenses 4a is 22 mm. Each of the optical axes A1 and the corresponding optical axis A2 are offset by 11 mm from each other in the Y direction, and therefore, the spacing Δ12 between optical axes A1 and A2 that are adjacent to each other in the Y direction is 11 mm.

The line sensors 5 and 6 have the same specifications. Regarding the line sensors 5 and 6, the pixel pitch is 3.5 μm, the number of pixels is 12257, and the effective length is 42.9 mm.

With the above-described design, fields of view F1 and F2 that are adjacent to each other overlap each other by 0.6 mm. Therefore, it is possible to observe an entire image-capturing area as wide as 44.6 mm seamlessly. In addition, because the spacing Δ1 between the optical axes A1 is larger than the width Di1 of each of the first images I1, the first images I1 that are adjacent to each other are completely spatially separated without overlapping each other. Similarly, the second images I2 that are adjacent to each other are completely spatially separated without overlapping each other.

Although, in this embodiment and the design example thereof, the objective lens groups 31 and 41 include the two objective lenses 3a and 4a, respectively, instead of this, the number of objective lenses 3a and the number of objective lenses 4a may be an arbitrary number equal to or larger than 3.

Although, in this embodiment and the design example thereof, each of the first deflecting element group and the second deflecting element group is composed of a combination of a plurality of prisms, instead of this, each of the first deflecting element group and the second deflecting element group may be composed of a plurality of mirrors.

Although, in this embodiment, the light emitted from the first objective lenses 3a and the light emitted from the second objective lenses 4a are separated into different planes by means of different positions of the prisms 11a and the prisms 11c, instead of this, the light emitted from the first objective lenses 3a and the light emitted from the second objective lenses 4a may be separated into different planes by means of different angles of light deflection performed by the prisms or the mirrors.

Third Embodiment

Next, an observation device 300 according to a third embodiment of the present invention will be described with reference to the drawings.

In this embodiment, configurations different from those in the first and second embodiments will be described. Also, configurations in common with those in the first and second embodiments will be denoted with the same reference signs and descriptions thereof will be omitted.

Figure 10:
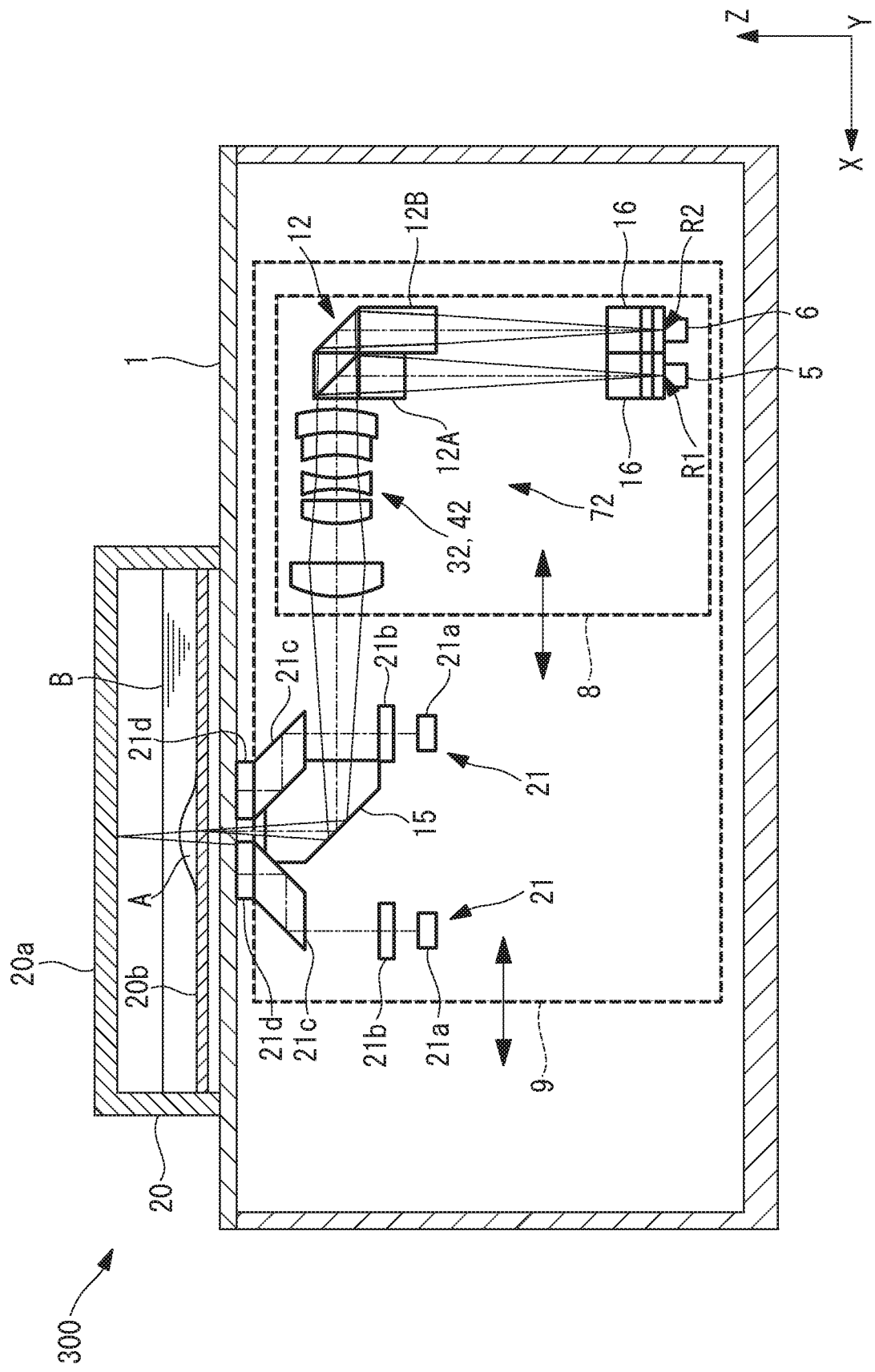
FIG. 10 is a longitudinal sectional view showing the overall configuration of an observation device according to a third embodiment of the present invention.

As shown in FIG. 10, the observation device 300 according to this embodiment includes the stage 1, the illumination optical systems 21, an image-capturing optical system 72, the focus adjusting mechanism 8, and the scanning mechanism 9. The observation device 300 is a modification of the observation device 200 according to the second embodiment and differs from the observation device 200 according to the second embodiment in the configuration of an optical-path separating optical system 12.

The image-capturing optical system 72 includes: a first objective lens group 32; a second objective lens group 42; the first line sensor 5; the second line sensor 6; and the optical-path separating optical system 12.

Figure 11:
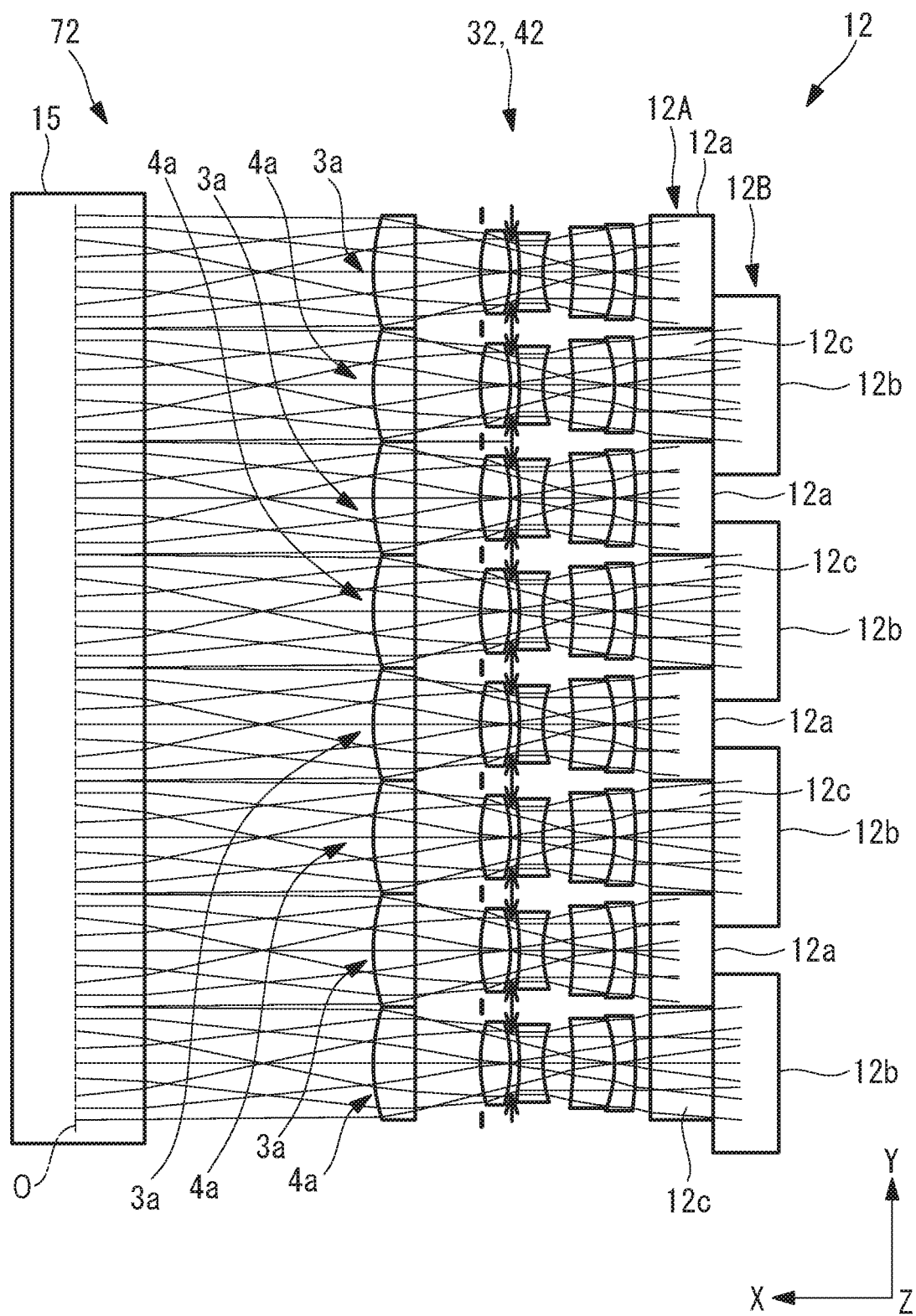
FIG. 11 is a top plan view in the Z direction of an image-capturing optical system of the observation device in FIG. 10.

As shown in FIG. 11, the first objective lens group 32 includes four first objective lenses 3a, and the second objective lens group 42 includes four second objective lenses 4a. The other configurations of the first objective lens group 32 and the second objective lens group 42 are the same as those of the first objective lens group 31 and the second objective lens group 41, respectively, in the second embodiment.

Figure 12A:
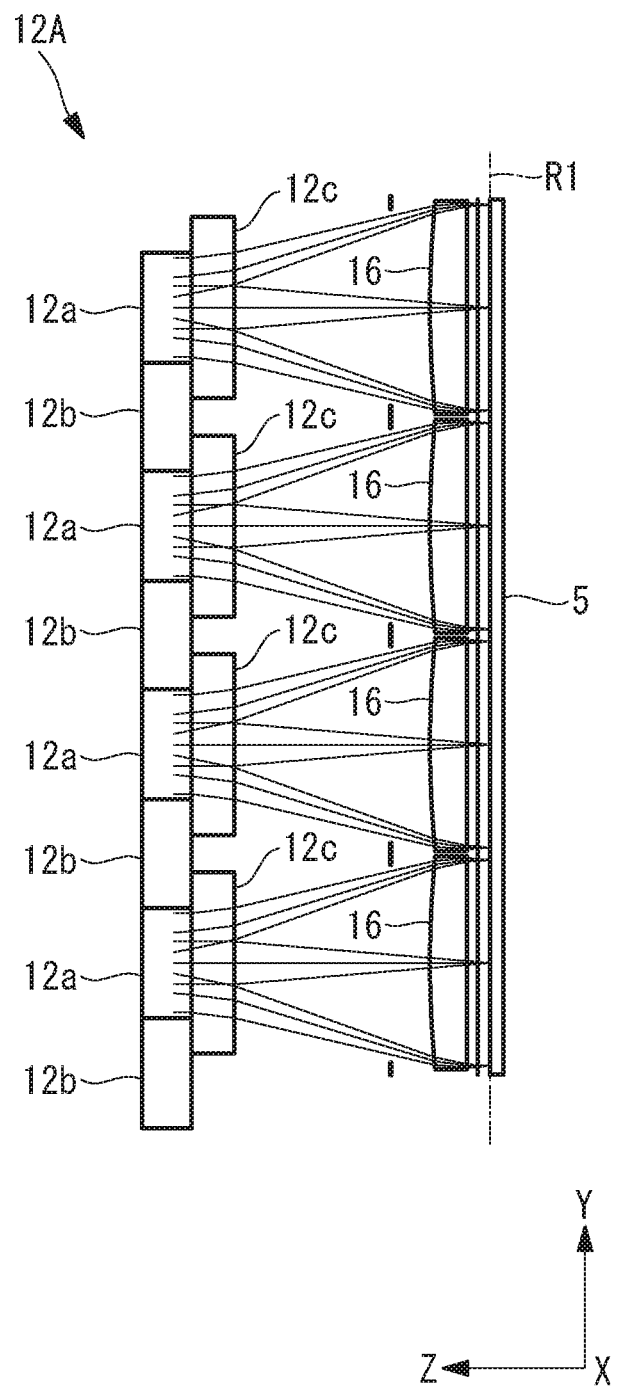
FIG. 12A is a side elevational view of a first prism group of an optical-path separating optical system of the image-capturing optical system in FIG. 10, as viewed from the right side along the X direction.
Figure 12B:
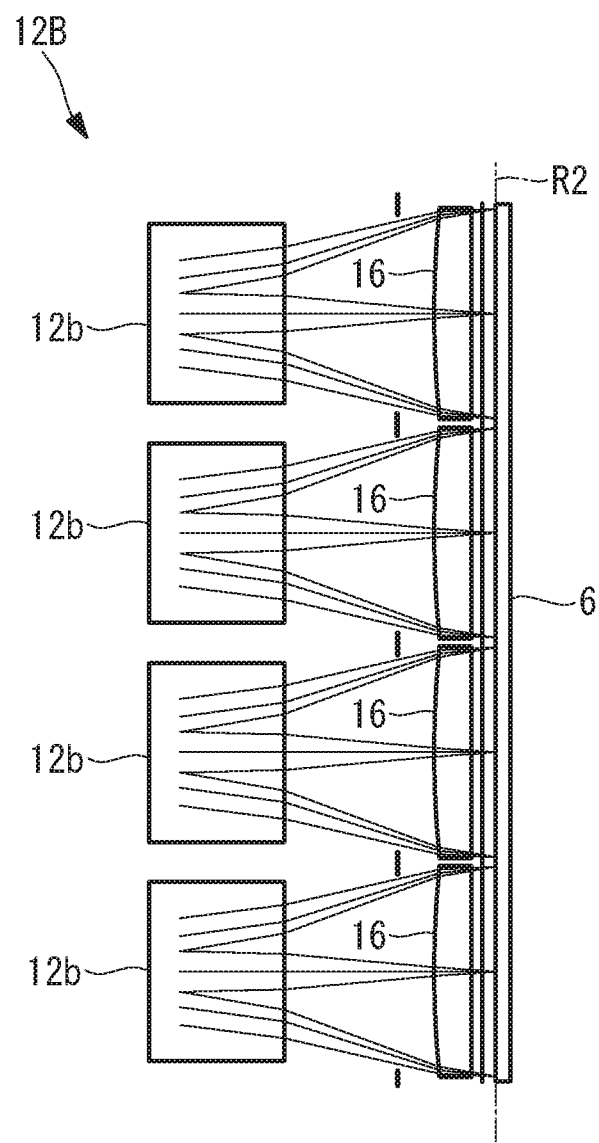
FIG. 12B is a side elevational view of a second prism group of the optical-path separating optical system of the image-capturing optical system in FIG. 10, as viewed from the right side along the X direction.

As shown in FIGS. 12A and 12B, the optical-path separating optical system 12 includes: a first prism group (first deflecting element group) 12A; and a second prism group (second deflecting element group) 12B.

As shown in FIG. 12A, the first prism group 12A includes four prisms 12a for deflecting, in the Z direction, the four light rays emitted along the X direction from the four first objective lenses 3a. As shown in FIG. 12B, the second prism group 12B includes four prisms 12b for deflecting, in the Z direction, the four light rays emitted along the X direction from the four second objective lenses 4a. Reference numeral 12c denotes parallel plates.

The four prisms 12a are arranged in the Y direction, and the four prisms 12b are arranged in the Y direction. In addition, the prisms 12a and the prisms 12b are disposed at positions that differ from each other in the X-direction. Therefore, the light emitted from the first objective lenses 3a and the light emitted from the second objective lenses 4a are separated by the prisms 12a and the prisms 12b into different planes that are separated from each other in the X direction.

The light deflected by the prisms 12a travels in the Z direction and forms first images I1 in the first image-forming region R1. The light deflected by the prisms 12b travels in the Z direction and forms second images I2 in the second image-forming region R2. Therefore, the first image-forming region R1 and the second image-forming region R2 are disposed at positions that are separated from each other in the X direction. In this embodiment, the first image-forming region R1 and the second image-forming region R2 are planar regions orthogonal to the Z direction. The first line sensor 5 is disposed in the first image-forming region R1 along the Y direction, and the second line sensor 6 is disposed in the second image-forming region R2 along the Y direction.

Here, although the air-equivalent length from each of the first objective lenses 3a to the corresponding field lens 16 and the air-equivalent length from each of the second objective lenses 4a to the corresponding field lens 16 are identical to each other, the sum of the glass length and the air gap of the first prism group 12A is shorter than the sum of the glass length and the air gap of the second prism group 12B. By doing so, the first image-forming region R1 and the second image-forming region R2 are disposed on the same plane.

This embodiment provides the following advantages, in addition to the advantages provided by the first and second embodiments. More specifically, this embodiment provides an advantage in that the image-capturing area can be enlarged in the main scanning direction by providing a larger number of objective lenses 3a and 4a than in the second embodiment. This embodiment provides another advantage in that because the two line sensors 5 and 6 are disposed on the same plane so as to be close to each other, the two line sensors 5 and 6 can be provided on the same substrate, whereby assembling can be made easier.

In this embodiment, the two line sensors 5 and 6 may be disposed at positions that differ from each other in the Z direction.

A design example of the image-capturing optical system 72 in this embodiment will be described below.

All of the objective lenses 3a and 4a have the same specifications. Regarding the objective lenses 3a and 4a, the magnification is 1.8, the NA (numerical aperture) is 0.11, the widths Df1 and Df2 of the fields of view F1 and F2 on the observation line O are 11.6 mm, and the widths Di1 and Di2 of the images I1 and I2 are 20.88 mm. The Y-direction spacing Δ1 between the optical axes A1 of neighboring first objective lenses 3a is 22 mm, and the Y-direction spacing Δ2 between the optical axes A2 of neighboring second objective lenses 4a is 22 mm. Each of the optical axes A1 and the corresponding optical axis A2 are offset by 11 mm from each other in the Y direction, and therefore, the spacing Δ12 between optical axes A1 and A2 that are adjacent to each other in the Y direction is 11 mm.

The line sensors 5 and 6 have the same specifications. Regarding the line sensors 5 and 6, the pixel pitch is 3.5 µm, the number of pixels is 24829, and the effective length is 86.9 mm.

With the above-described design, fields of view F1 and F2 that are adjacent to each other overlap each other by 0.6 mm. Therefore, it is possible to observe an entire image-capturing area as wide as 88.6 mm seamlessly. In addition, because the spacing Δ1 between neighboring optical axes A1 is larger than the width Di1 of each of the first images I1, first images I1 that are adjacent to each other are completely spatially separated without overlapping each other. Similarly, second images I2 that are adjacent to each other are completely spatially separated without overlapping each other.

Fourth Embodiment

Next, an observation device 400 according to a fourth embodiment of the present invention will be described with reference to the drawings.

In this embodiment, configurations different from those in the first to third embodiments will be described. Also, configurations in common with those in the first to third embodiments will be denoted with the same reference signs and descriptions thereof will be omitted.

Figure 13:
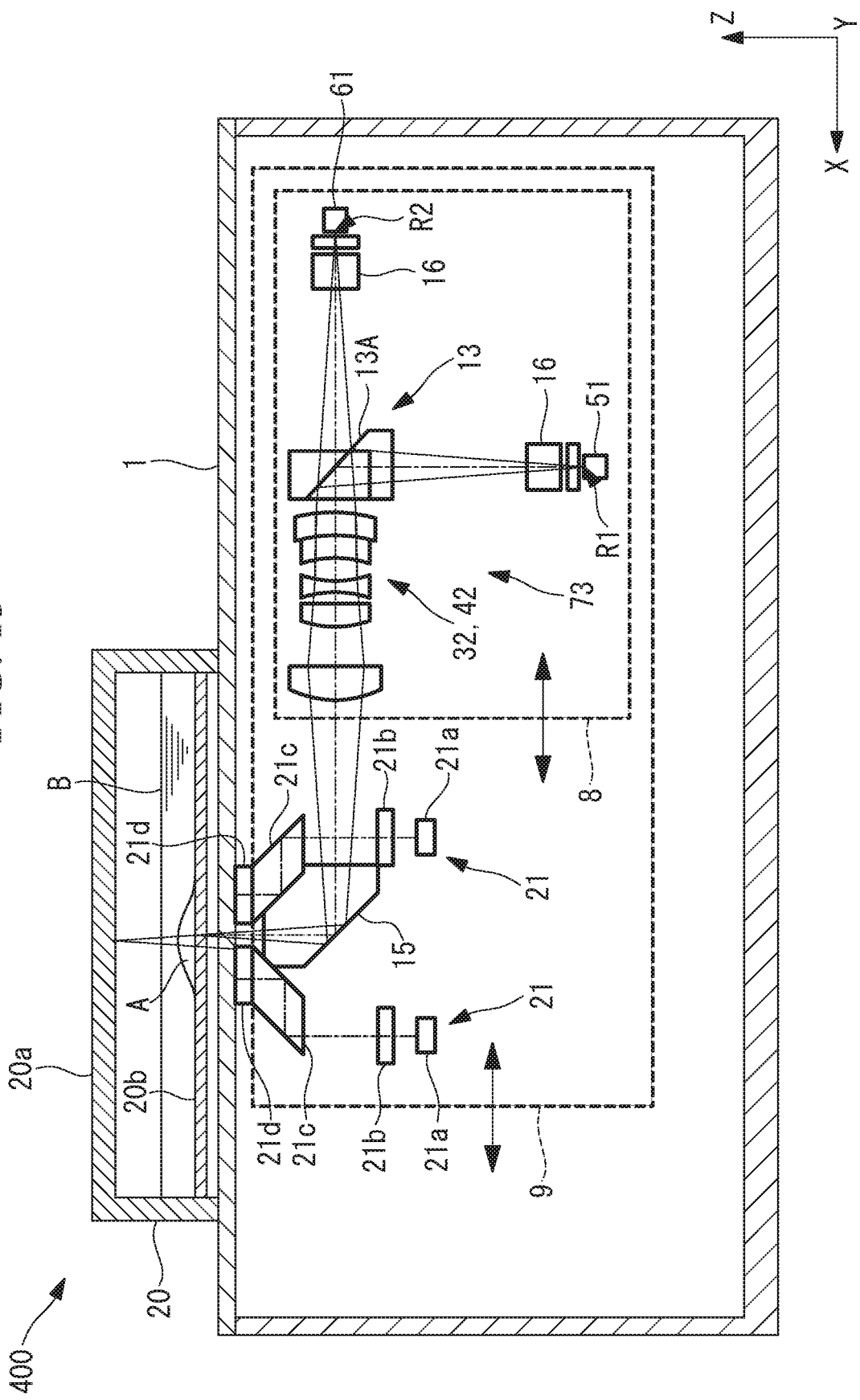
FIG. 13 is a longitudinal sectional view showing the overall configuration of an observation device according to a fourth embodiment of the present invention.

As shown in FIG. 13, the observation device 400 according to this embodiment includes the stage 1, the illumination optical systems 21, an image-capturing optical system 73, the focus adjusting mechanism 8, and the scanning mechanism 9. The observation device 400 is a modification of the observation device 200 according to the second embodiment and differs from the observation device 200 according to the second embodiment in the configuration of an optical-path separating optical system 13.

Figure 14:
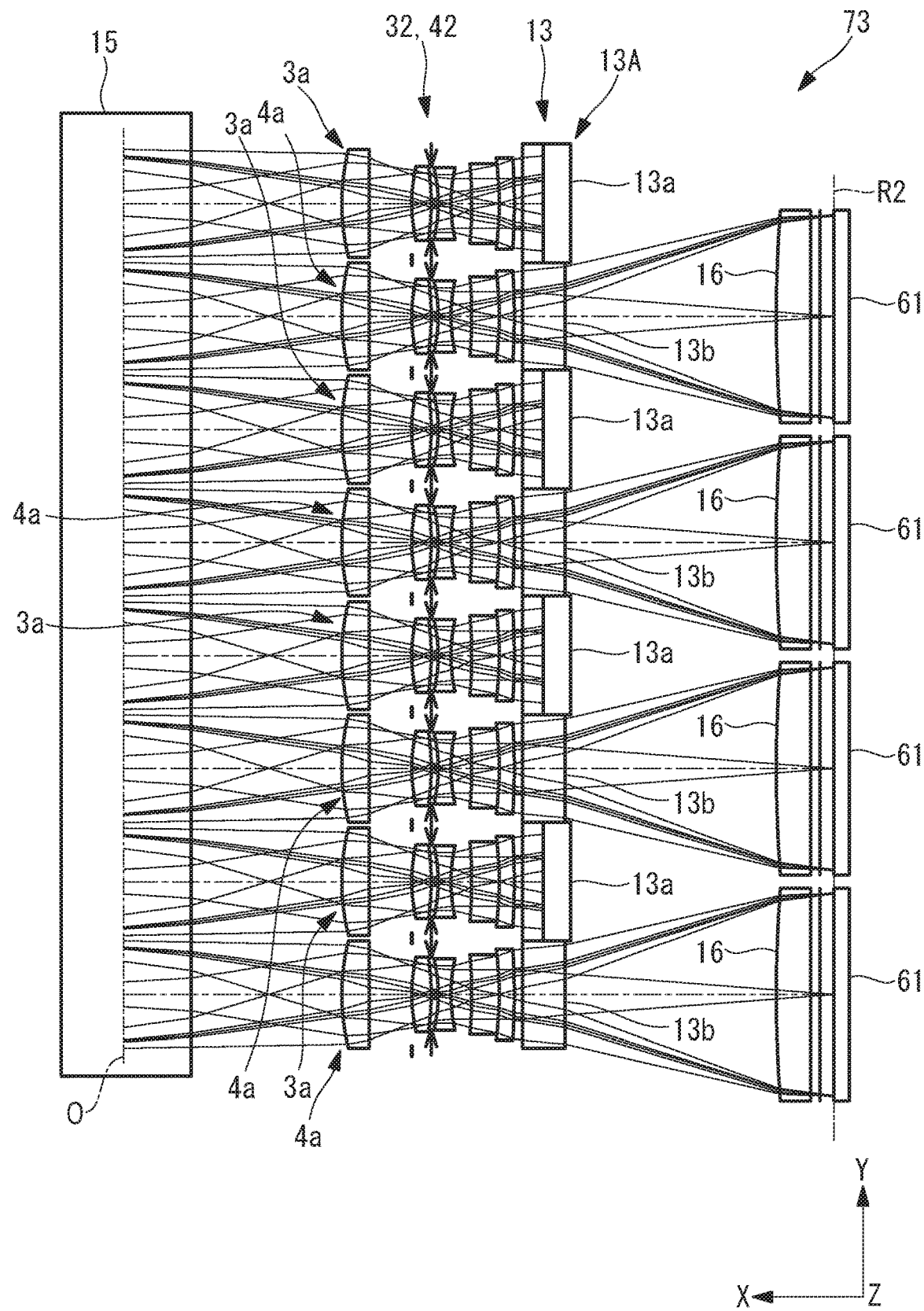
FIG. 14 is a top plan view in the Z direction of an image-capturing optical system of the observation device in FIG. 13.

As shown in FIG. 14, the image-capturing optical system 73 includes: the first objective lens group 32; the second objective lens group 42; four first line sensors 51; four second line sensors 61; and the optical-path separating optical system 13.

Figure 15:
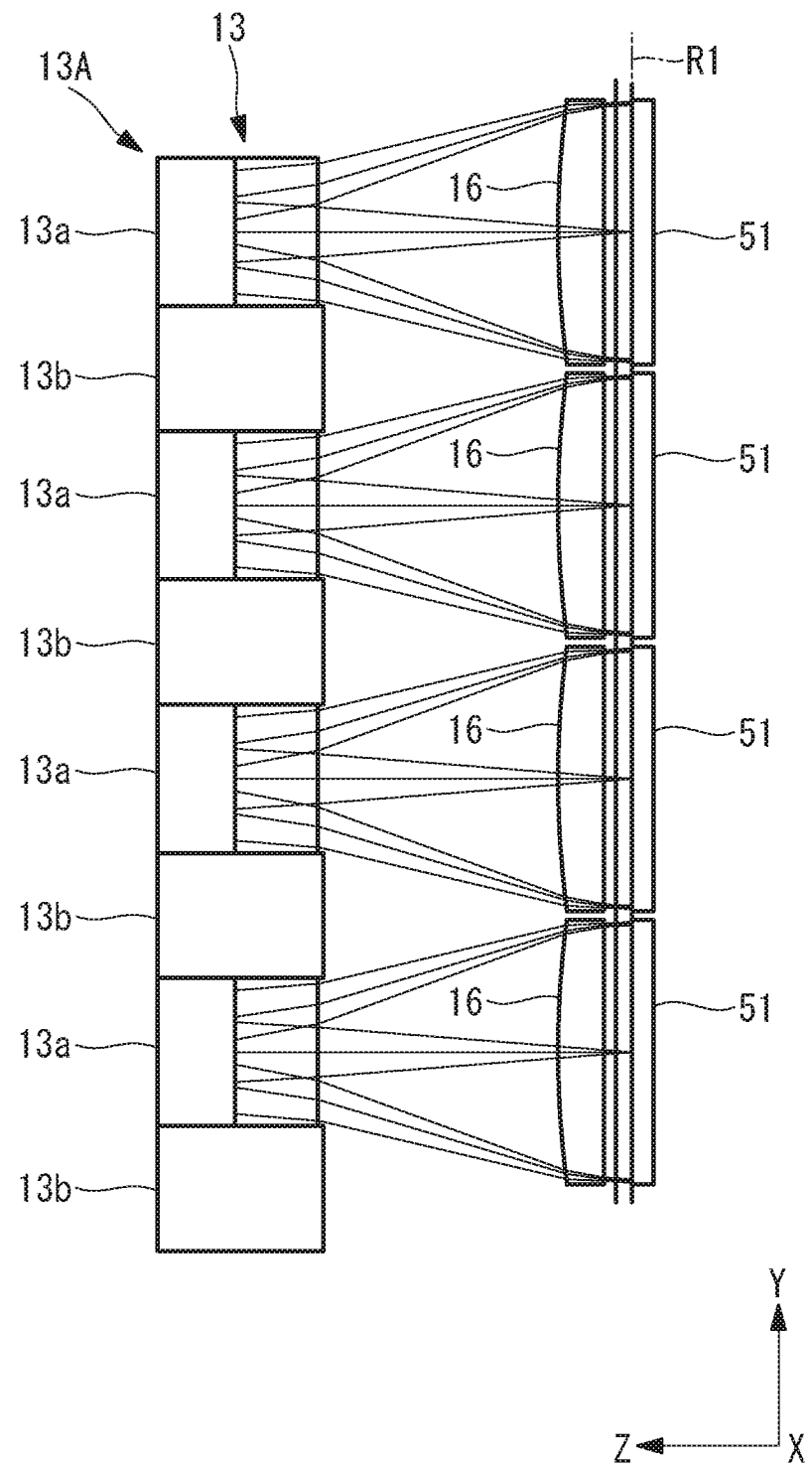
FIG. 15 is a side elevational view of an optical-path separating optical system of the image-capturing optical system in FIG. 13, as viewed from the right side along the X direction.

As shown in FIG. 15, the optical-path separating optical system 13 includes a single prism group 13A. The prism group 13A includes four prisms 13a for deflecting, in the Z direction, the four light rays emitted along the X direction from the four first objective lenses 3a. Reference numeral 13b denotes parallel plates.

The four prisms 13a are arranged in a row in the Y direction. No prisms are present between each of the second objective lenses 4a and the corresponding line sensor 61, and the light emitted from the second objective lenses 4a travels along the X direction. Therefore, the light emitted from the first objective lenses 3a and the light emitted from the second objective lenses 4a are separated by the prisms 13a into different planes that are orthogonal to each other.

The light that is emitted from the first objective lenses 3a and is then deflected by the prisms 13a travels in the Z direction and forms first images I1 in the first image-forming region R1. The light emitted from the second objective lenses 4a forms second images I2 in the second image-forming region R2. Therefore, in this embodiment, the first image-forming region R1 is a planar region orthogonal to the Z direction, and the second image-forming region R2 is a planar region orthogonal to the X direction. In this manner, the first image-forming region R1 and the second image-forming region R2 are disposed at positions that are sepa-rated from each other, i.e., the positions in the Z direction and the X direction between the region R1 and the region R2 are different from each other. Each of the first line sensors 51 is disposed along the Y direction in the first image-forming region R1, and each of the second line sensors 61 is disposed along the Y direction in the second image-forming region R2.

In this embodiment, one first line sensor 51 is provided for one first objective lens 3a, and one second line sensor 61 is provided for one second objective lens 4a. Each of the first line sensors 51 captures one first image I1, and each of the second line sensors 61 captures one second image I2.

This embodiment provides the following advantages, in addition to the advantages provided by the first and second embodiments. More specifically, this embodiment provides an advantage in that the image-capturing area can be enlarged in the Y direction by providing a larger number of objective lenses 3a and 4a than in the second embodiment. In addition, no long line sensors are required as a result of the objective lenses 3a and 4a being provided with single line sensors 51 and 61, respectively. This affords an advantage in that line sensors 51 and 61 having high yield and low price can be used.

A design example of the image-capturing optical system 73 in this embodiment will be described below.

All of the objective lenses 3a and 4a have the same specifications. Regarding the objective lenses 3a and 4a, the magnification is 1.8, the NA (numerical aperture) is 0.11, the widths Df1 and Df2 of the fields of view F1 and F2 on the observation line O are 11.6 mm, and the widths Di1 and Di2 of the images I1 and I2 are 20.88 mm. The Y-direction spacing Δ1 between the optical axes A1 of neighboring first objective lenses 3a is 22 mm, and the Y-direction spacing Δ2 between the optical axes A2 of neighboring second objective lenses 4a is 22 mm. Each of the optical axes A1 and the corresponding optical axis A2 are offset by 11 mm from each other in the Y direction, and therefore, the spacing Δ12 between optical axes A1 and A2 that are adjacent to each other in the Y direction is 11 mm.

The line sensors 5 and 6 have the same specifications. Regarding the line sensors 5 and 6, the pixel pitch is 3.5 µm, the number of pixels is 24829, and the effective length is 86.9 mm.

With the above-described design, fields of view F1 and F2 that are adjacent to each other overlap each other by 0.6 mm. Therefore, it is possible to observe an entire image-capturing area as wide as 88.6 mm seamlessly. In addition, because the spacing Δ1 between neighboring optical axes A1 is larger than the width Di1 of each of the first images I1, first images I1 that are adjacent to each other are completely spatially separated without overlapping each other. Similarly, second images I2 that are adjacent to each other are completely spatially separated without overlapping each other.

Although the cells A are observed with the observation devices 100, 200, 300, and 400 in the above-described first to fourth embodiments, specimens that are observed with the observation devices 100, 200, 300, and 400 may be anything other than the cells A.

Although light passing through the specimen is observed in the above-described first to fourth embodiments, instead of this, light reflected at the specimen or light (e.g., fluorescence) generated by the specimen may be observed.

Although, in the above-described first to fourth embodiments, the illumination optical systems 2 and 21 are disposed on the same side of the stage 1 as the side on which the image-capturing optical systems 7, 71, 72, and 73 are disposed, the illumination optical systems 2 and 21 may be disposed at other locations. For example, the illumination optical systems 2 and 21 may be disposed above the stage 1 or laterally to the stage 1.

Although, in the above-described first to fourth embodiments, the illumination optical systems 2 and 21 are provided in the observation devices 100, 200, 300, and 400, an independent illumination optical system separated from the observation devices 100, 200, 300, and 400 may irradiate the specimen with illumination light. For example, the illumination optical systems may be fixed to the interior of the cell culture device.

Although line sensors are used as the image capturing elements 5, 6, 51, and 61 in the above-described first to fourth embodiments, instead of this, a two-dimensional image capturing element having a plurality of rows of pixels may be used.

The above-described embodiment also leads to the following aspects.

One aspect of the present invention is an observation device including: a first objective optical system group that has a plurality of first objective optical systems arranged in a row so as to be parallel to one another, wherein each of the plurality of first objective optical systems forms a first image of light coming from a first field of view on an observation line; a second objective optical system group that has a plurality of second objective optical systems arranged in a row so as to be parallel to one another, wherein each of the plurality of second objective optical systems forms a second image of light coming from a second field of view on the observation line; a first image capturing element for capturing plurality of first images formed by the plurality of first objective optical systems; and a second image capturing element for capturing plurality of second images formed by the plurality of second objective optical systems, wherein each of the plurality of first objective optical systems and the plurality of second objective optical systems is a magnifying objective optical system having a magnification larger than 1, first fields of view and second fields of view are arranged alternately in a row on the observation line, and the plurality of first images are arranged in a row in a first image-forming region, the plurality of second images are arranged in a row in a second image-forming region, and the first image-forming region and the second image-forming region are disposed at positions that differ from each other.

According to this aspect, because the plurality of first objective optical systems of the first objective optical system group are arranged in a row so as to be parallel to one another, the plurality of first fields of view of the plurality of first objective optical systems are arranged in a row, and the plurality of first images formed by the plurality of first objective optical systems are arranged in a row. Furthermore, because the plurality of second objective optical systems of the second objective optical system group are arranged in a row so as to be parallel to one another, the plurality of second fields of view of the plurality of second objective optical systems are arranged in a row, and the plurality of second images formed by the plurality of second objective optical systems are arranged in a row.

The first fields of view and the second fields of view are alternately arranged on the same observation line. Therefore, an image of an elongated image-capturing area along the observation line can be acquired by joining the images of the first fields of view acquired by the first image capturing element and the images of the second fields of view acquired by the second image capturing element. In addition, images of a wide area can be acquired in a short time period by moving an examination subject and the observation line relatively to each other in a direction intersecting a longitudinal direction of the observation line and then repeating image capturing at a plurality of positions by means of the first image capturing element and the second image capturing element.

In this case, because the plurality of objective optical systems are used to capture images of the elongated image-capturing area along the observation line, the distance from the observation line to each of the image capturing elements becomes shorter than in the case where a single objective optical system is used, and the observation device can be made compact.

Furthermore, because the first objective optical systems and the second objective optical systems are magnifying objective optical systems, high-resolution first images and second images can be formed. Therefore, high-resolution images can be acquired.

Furthermore, because the first image-forming region in which the first images are formed and the second image-forming region in which the second images are formed differ from each other, a plurality of first images that are spatially separated from one another can be captured by the first image capturing element, and a plurality of second images that are spatially separated from one another can be captured by the second image capturing element. In other words, each of the spacing between two neighboring first images in the first image-forming region and the spacing between two neighboring second images in the second image-forming region is larger than the spacing between each of the first fields of view and a second field of view that is adjacent thereto on the observation line. By doing so, the first images, which are larger than the respective first fields of view, can be arranged in the first image-forming region without overlapping each other, and the second images, which are larger than the respective second fields of view, can be arranged in the second image-forming region without overlapping each other.

In the above-described aspect, the first image capturing element may be a first line sensor having a plurality of pixels arranged in a row, the second image capturing element may be a second line sensor having a plurality of pixels arranged in a row, the plurality of first objective optical systems may be arranged in a direction along a longitudinal direction of the first line sensor, and the plurality of second objective optical systems may be arranged in a direction along a longitudinal direction of the second line sensor.

With this configuration, the optical path from the first objective optical system group to the first line sensor can be configured from simple optical systems, and the optical path from the second objective optical system group to the second line sensor can be configured from simple optical systems.

In the above-described aspect, among the first fields of view and the second fields of view, the first field of view and the second field of view that is adjacent thereto may partially overlap each other.

With this configuration, images of an object on the observation line can be acquired seamlessly in a direction along the observation line.

The above-described aspect may further include: a light dividing element disposed between the observation line, and the first and second objective optical system groups, wherein the first objective optical system group and the second objective optical system group may be disposed in regions that differ from each other, and the light dividing element may split, into two light rays, light coming from the observation line and may divide the two light rays to the first objective optical system group and the second objective optical system group.

With this configuration, light from the image-capturing area along the observation line can be divided to both of the first objective optical system group and the second objective optical system group that are disposed in regions different from each other.

The above-described aspect may further include: an optical-path separating optical system disposed between the first and second objective optical system groups, and the first and second image capturing elements, wherein the first objective optical systems and the second objective optical systems may be arranged alternately in a row on the same plane, and the optical-path separating optical system may separate, into different planes, light coming from the plurality of first objective optical systems and light coming from the plurality of second objective optical systems.

With this configuration, the first objective optical systems and the second objective optical systems are alternately disposed in a row in the same manner as the first fields of view and the second fields of view on the observation line. By doing so, the optical paths from the observation line to the first and second objective optical system groups can be configured from simple optical systems.

Furthermore, light emitted from the first objective optical systems and light emitted from the second objective optical systems are alternately arranged on the same plane just after the first and second objective optical system groups. The first images and the second images can be formed in image-forming regions that differ from each other by separating, into different planes, light emitted from the first objective optical systems and light emitted from the second objective optical systems by means of the optical-path separating optical system.

In the above-described aspect, the optical-path separating optical system may include a first deflecting element group for deflecting the light coming from the plurality of first objective optical systems and a second deflecting element group for deflecting the light coming from the plurality of second objective optical systems, and the first deflecting element group and the second deflecting element group may be disposed at positions that differ from each other or may deflect light at angles that differ from each other.

With this configuration, the optical-path separating optical system can be realized with a simple configuration.

The above-described aspect may further include: a stage for supporting a specimen; and an illumination optical system for irradiating the specimen supported by the stage with illumination light, wherein the first objective optical system group, the second objective optical system group, the first image capturing element, the second image capturing element, and the illumination optical system may be disposed on the same side of the stage.

The observation device can be made thin by disposing the objective optical system groups and the image capturing elements required to capture images of the specimen and the illumination optical system required to illuminate the specimen on the same side of the stage.

The above-described aspect may further include: a scanning mechanism for integrally moving the first objective optical system group, the second objective optical system group, the first image capturing element, and the second image capturing element in a direction intersecting the observation line.

With this configuration, the image-capturing area can be enlarged in a direction intersecting the observation line.

When the above-described illumination optical system is included, the scanning mechanism may integrally move the illumination optical system, as well as the first objective optical system group, the second objective optical system group, the first image capturing element, and the second image capturing element.

The above-described aspect may further include: a focus adjusting mechanism for integrally moving the first objective optical system group, the second objective optical system group, the first image capturing element, and the second image capturing element in a direction along the optical axes of the plurality of first objective optical systems and the plurality of second objective optical systems.

As a result of the first and second objective optical system groups moving in a direction along the optical axes of the first and second objective optical systems, the focal position of each of the objective optical systems, i.e., the position of the observation line moves in a direction along the optical axes. By doing so, the focal point of each of the objective optical systems can be aligned with the specimen supported on the stage. In addition, the first and second images also move as the first and second objective optical system groups move. As a result of the first and second image capturing elements also moving in a direction along the optical axes integrally with the first and second objective optical systems, a sharp image of the specimen can be acquired by the first and second image capturing elements.

REFERENCE SIGNS LIST 100, 200, 300, 400 Observation device
1 Stage
2 Illumination optical system
3, 31, 32 First objective lens group (first objective optical system group)
3a First objective lens (first objective optical system)
4, 41, 42 Second objective lens group (second objective optical system group)
4a Second objective lens (second objective optical system)
5, 51 First line sensor (first image capturing element)
6, 61 Second line sensor (second image capturing element)
7, 71, 72, 73 Image-capturing optical system
8 Focus adjusting mechanism
9 Scanning mechanism
10 Light dividing element
11, 12, 13 Optical-path separating optical system
A Cell (specimen)
F1 First field of view
F2 Second field of view
I1 First image
I2 Second image
O Observation line
R1 First image-forming region
R2 Second image-forming region

The invention claimed is:
1. An observation device comprising:
a first objective lens group that has a plurality of first objective lenses arranged in a row so as to be parallel to one another, wherein each of the plurality of first objective lenses forms a first image of light coming from a first field of view on an observation line;
a second objective lens group that has a plurality of second objective lenses arranged in a row so as to be parallel to one another, wherein each of the plurality of second objective lenses forms a second image of light coming from a second field of view on the observation line;

a first image capturing element for capturing plurality of first images formed by the plurality of first objective lenses; and a second image capturing element for capturing plurality of second images formed by the plurality of second objective lenses, wherein each of the plurality of first objective lenses and the plurality of second objective lenses is a magnifying objective lens having a magnification larger than 1, a first axis of light incident on the plurality of first objective lenses and a second axis of light incident on the plurality of second objective lenses are parallel to one another, first fields of view and second fields of view are arranged alternately in a row on the observation line, and the plurality of first images are arranged in a row in a first image-forming region, the plurality of second images are arranged in a row in a second image-forming region, and the first image-forming region and the second image-forming region are disposed at positions that differ from each other.

2. The observation device according to claim 1, wherein the first image capturing element is a first line sensor having a plurality of pixels arranged in a row, the second image capturing element is a second line sensor having a plurality of pixels arranged in a row, the plurality of first objective lenses are arranged in a direction along a longitudinal direction of the first line sensor, and the plurality of second objective lenses are arranged in a direction along a longitudinal direction of the second line sensor.

3. The observation device according to claim 1, wherein, among the first fields of view and the second fields of view, the first field of view and the second field of view that is adjacent thereto partially overlap each other.

4. The observation device according to claim 1, further comprising:

a divider disposed between the observation line, and the first and second objective lens groups, wherein the first objective lens group and the second objective lens group are disposed in regions that differ from each other, and the divider splits, into two light rays, light coming from the observation line and divides the two light rays to the first objective lens group and the second objective lens group.

5. The observation device according to claim 1, further comprising:

a separator disposed between the first and second objective lens groups, and the first and second image capturing elements, wherein the first objective lenses and the second objective lenses are arranged alternately in a row on the same plane, and the separator separates, into different planes, light coming from the plurality of first objective lenses and light coming from the plurality of second objective lenses.

6. The observation device according to claim 5, wherein the separator includes a first prism group for deflecting the light coming from the plurality of first objective lenses and a second prism group for deflecting the light coming from the plurality of second objective lenses, and the first prism group and the second prism group are disposed at positions that differ from each other or deflect light at angles that differ from each other.

7. The observation device according to claim 1, further comprising:

a stage for supporting a specimen; and an illumination optical system that comprises a light source and that irradiates the specimen supported by the stage with illumination light, wherein the first objective lens group, the second objective lens group, the first image capturing element, the second image capturing element, and the illumination optical system are disposed on the same side of the stage.

8. The observation device according to claim 1, further comprising:

a scanning mechanism for integrally moving the first objective lens group, the second objective lens group, the first image capturing element, and the second image capturing element in a direction intersecting the observation line.

9. The observation device according to claim 1, further comprising:

a focus adjusting mechanism for integrally moving the first objective lens group, the second objective lens group, the first image capturing element, and the second image capturing element in a direction along the optical axes of the plurality of first objective lenses and the plurality of second objective lenses.

10. The observation device according to claim 1, further comprising:

an illumination optical system that comprises a light source, wherein illumination light emitted from the illumination optical system is incident on a specimen from obliquely above.

11. The observation device according to claim 1, wherein the first fields of view and the second fields of view are arranged so that spacing between neighboring axes of the first fields of view is larger than width of each of the plurality of first images in a main scanning direction, and spacing between neighboring axes of the second fields of view is larger than width of each of the plurality of second images in the main scanning direction.

* * * * *